United States Patent
Sankar

(10) Patent No.: US 9,277,901 B2
(45) Date of Patent: *Mar. 8, 2016

(54) PULSE COMPRESSION SYSTEMS AND METHODS

(71) Applicant: Scidea Research, Inc., Tustin, CA (US)

(72) Inventor: Pat Sankar, Tustin, CA (US)

(73) Assignee: Scidea Research, Inc., Tustin, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/541,919

(22) Filed: Nov. 14, 2014

(65) Prior Publication Data

US 2015/0196272 A1    Jul. 16, 2015

Related U.S. Application Data

(63) Continuation of application No. 14/066,608, filed on Oct. 29, 2013, now Pat. No. 8,974,390.

(60) Provisional application No. 61/886,582, filed on Oct. 3, 2013.

(51) Int. Cl.

| | |
|---|---|
| *A61B 8/00* | (2006.01) |
| *A61B 8/14* | (2006.01) |
| *G01S 7/52* | (2006.01) |
| *G01S 7/484* | (2006.01) |
| *G01S 7/524* | (2006.01) |
| *G01S 13/28* | (2006.01) |

(Continued)

(52) U.S. Cl.

CPC .................. *A61B 8/14* (2013.01); *A61B 8/5207* (2013.01); *A61B 8/54* (2013.01); *G01S 7/04* (2013.01); *G01S 7/484* (2013.01); *G01S 7/5202* (2013.01); *G01S 7/52003* (2013.01); *G01S 7/524* (2013.01); *G01S 7/52046* (2013.01); *G01S 7/56* (2013.01); *G01S 13/28* (2013.01); *G01S 13/89* (2013.01); *G01S 15/102* (2013.01); *G01S 15/89* (2013.01); *G01S 15/8961* (2013.01); *G01S 17/102* (2013.01); *G01S 13/885* (2013.01); *G01S 13/90* (2013.01)

(58) Field of Classification Search
CPC ........... A61B 8/00; G01S 7/52; G01S 7/5202; G01S 17/10; G01S 7/282
See application file for complete search history.

(56) References Cited

U.S. PATENT DOCUMENTS

| | | |
|---|---|---|
| 2,939,017 A | 5/1960 | Teague, Jr. et al. |
| 4,318,019 A | 3/1982 | Teasley et al. |

(Continued)

FOREIGN PATENT DOCUMENTS

RU            2367068          9/2009

OTHER PUBLICATIONS

U.S. Appl. No. 13/945,126, including its prosecution history, the cited references, and the Office Actions therein, filed Jul. 18, 2013, Sankar.

(Continued)

*Primary Examiner* — Joel Lamprecht
(74) *Attorney, Agent, or Firm* — Knobbe, Martens, Olson & Bear, LLP

(57) ABSTRACT

Systems and methods of optimal pulse compression are described. A method of determining an optimal pulse takes as an input a function of the impulse response of a transducer and produces a pulse optimized for transmission through that transducer. Images then produced with that transducer will have both superior range and spatial resolution.

20 Claims, 31 Drawing Sheets

(51) Int. Cl.

| | |
|---|---|
| *G01S 15/10* | (2006.01) |
| *G01S 15/89* | (2006.01) |
| *G01S 17/10* | (2006.01) |
| *A61B 8/08* | (2006.01) |
| *G01S 7/04* | (2006.01) |
| *G01S 7/56* | (2006.01) |
| *G01S 13/89* | (2006.01) |
| *G01S 13/88* | (2006.01) |
| *G01S 13/90* | (2006.01) |

(56) References Cited

U.S. PATENT DOCUMENTS

| | | |
|---|---|---|
| 4,851,848 A | 7/1989 | Wehner |
| 4,973,967 A | 11/1990 | David et al. |
| 5,315,159 A | 5/1994 | Gribnau |
| 5,387,918 A | 2/1995 | Wiesbeck et al. |
| 5,719,579 A | 2/1998 | Torre et al. |
| 5,808,580 A | 9/1998 | Andrews, Jr. |
| 6,142,942 A | 11/2000 | Clark |
| 6,188,147 B1 | 2/2001 | Hazelton et al. |
| 7,042,109 B2 | 5/2006 | Gabrys |
| 7,358,624 B2 | 4/2008 | Bacon |
| 7,425,772 B2 | 9/2008 | Novo Vidal |
| 7,652,389 B2 | 1/2010 | Farmer |
| 7,679,210 B2 | 3/2010 | Zhu |
| 7,715,166 B2 | 5/2010 | Schultz et al. |
| 7,841,982 B2 | 11/2010 | Johnson et al. |
| 8,009,001 B1 | 8/2011 | Cleveland |
| 8,035,551 B1 | 10/2011 | Govoni |
| 8,049,663 B2 | 11/2011 | Frank et al. |
| 8,264,314 B2 | 9/2012 | Sankar |
| 8,514,045 B2 | 8/2013 | Sankar |
| 8,514,047 B2 | 8/2013 | Sankar |
| 8,625,643 B2 | 1/2014 | Sankar |
| 8,974,390 B1 * | 3/2015 | Sankar .................. 600/437 |
| 2005/0033170 A1 | 2/2005 | Angelsen et al. |
| 2008/0013245 A1 | 1/2008 | Schultz et al. |
| 2008/0074223 A1 | 3/2008 | Pribonic |
| 2008/0084071 A1 | 4/2008 | Zhu |
| 2008/0231052 A1 | 9/2008 | Farmer |
| 2008/0315709 A1 | 12/2008 | Uchiyama |
| 2010/0133853 A1 | 6/2010 | Masi et al. |
| 2011/0031760 A1 | 2/2011 | Lugg |
| 2011/0241349 A1 | 10/2011 | Sankar |
| 2012/0209113 A1 | 8/2012 | Sankar |

OTHER PUBLICATIONS

U.S. Appl. No. 14/147,262, including its prosecution history, the cited references, and the Office Actions therein, filed Jan. 3, 2014, Sankar.

U.S. Appl. No. 13/657,736, including its prosecution history, the cited references, and the Office Actions therein, filed Oct. 22, 2012, Sankar.

International Search Report mailed by the Russian Patent Office on Nov. 21, 2013 in the corresponding PCT Application No. PCT/US2013/054725 (7 pages).

"Generating Nonlinear FM Chrip Waveforms for Radar," Sandia National Laboratories, 34 pages, Sep. 2006.

* cited by examiner

TYPICAL FAN SHAPED BEAM
AS USED ON IMAGING SONARS

PULSE COMPRESSION SYSTEMS AND METHODS

CROSS-REFERENCE TO RELATED APPLICATIONS

Any and all applications for which a foreign or domestic priority claim is identified in the Application Data Sheet as filed with the present application, are hereby incorporated by reference under 37 CFR 1.57. The present application is a continuation of U.S. patent application Ser. No. 14/066,608, filed Oct. 29, 2013 and titled "PULSE COMPRESSION SYSTEMS AND METHODS," which claims the benefit of U.S. Provisional Application No. 61/886,582, filed Oct. 3, 2013 and titled "METHOD OF PULSE COMPRESSION." The entire disclosure of each of the foregoing applications is hereby incorporated herein by reference in their entireties.

BACKGROUND

1. Field

The disclosure generally relates to systems and devices, including imaging systems and devices, that transmit or receive analog signals, such as RADAR, LIDAR, SONAR, ultrasounds, MRI, and the like, and to methods of improving resolution with pulse compression techniques.

2. Description of the Related Art

Various techniques for pulse compression are known in the art. However, conventional techniques have various limitations and disadvantages.

SUMMARY

Pulse compression is a technique for improving the resolution of imaging devices that transmit or receive analog signals (such as RADAR, ultrasound, MRI, CT etc.). The rectangular pulse given in equation (1) is the base pulse with no compression applied. The most popular pulse compression is to use Linear Frequency Modulation to generate a chirp signal (see equation 2).

$$S_{REC}(n) = A \exp(-j2\pi f_c n) T/2 \leq n < T \quad (1)$$

$$S_{CHIRP}(n) = A \exp(-j2\pi f_c n^2) T/2 \leq n < T \quad (2)$$

Though the chirp signal has a very good pulse compression, the advantages it provides of improved range or spatial resolution can be limited by the bandwidth of a transducer used in the system.

Generally, a signal transmission system, an imaging system, or other pulse compression systems include a signal generator that generates a desired signal that is passed through a transducer and/or other components of the system. The transducer and/or other components can have electromechanical impulse responses that will affect the signal, modifying it from its original, desired form. These modifications can adversely impact the resolution, range, or other characteristics of the system. Various embodiments described herein relate to methods and systems for designing an optimal pulse best suited for any given transducer or combination of transducers and/or other components. An optimal pulse can account for the properties of these various components and the effect that they have on a signal.

In various embodiments, for example, an imaging system can include an operations component configured to receive a first digital signal, convert the first digital signal into an analog signal and transmit the analog signal toward a target, receive a reflected signal from the target, and convert the reflected signal into a second digital signal. The operations component can have an impulse response function that reflects the properties of the operations component and its ability to affect a signal passing through the operations component. The imaging system can also include a processor configured to correlate the second digital signal with the first digital signal in order to generate an image and a pulse generator configured to receive an input comprising the impulse response function of the operations component and to generate the first digital signal based on the input. In some embodiments, the imaging system can further include a display configured to display the image.

In some embodiments, the operations component can include a first transducer configured to convert the first digital signal to the analog signal and transmit the analog signal toward the target, and the first transducer can have a first transducer impulse response function that reflects the properties of the first transducer and its ability to affect a signal passing through the first transducer. In some embodiments, the first transducer can be configured to receive the reflected signal from the target and convert the reflected signal into the second digital signal. In some embodiments, the impulse response function of the operations component comprises the first transducer impulse response function convolved with itself. In some embodiments, the operations component can include a second transducer configured to receive the reflected signal from the target and convert the reflected signal into the second digital signal, and the second transducer can have a second transducer impulse response function that reflects the properties of the second transducer and its ability to affect a signal passing through the second transducer. In some embodiments the impulse response function of the operations module is the first transducer impulse response function convolved with the second transducer impulse response function.

In some embodiments, the analog signal transmitted toward a target can be an electromagnetic signal. In some embodiments, the analog signal can be a mechanical signal, such as a sonar or ultrasound signal. In some embodiments, the imaging system can be a radar system. In some embodiments, the imaging system can be an ultrasound system.

In various embodiments, an ultrasound-based diagnostic medical imaging system can include a transducer configured to be placed adjacent a tissue surface, the transducer comprising a piezoelectric crystal configured to produce ultrasound waves for transmission into the tissue surface, the transducer configured to receive ultrasound waves reflected from structures below the tissue surface and convert the reflected ultrasound waves into a digital received signal, wherein an impulse response function of the transducer reflects the properties of the transducer and its ability to affect a signal passing through the transducer. The ultrasound-based diagnostic medical imaging system can also include a signal generator configured to generate an optimized output signal configured to account for the impulse response function of the transducer, the signal generator configured to access an input based on the impulse response function of the transducer in order to generate the optimized output signal. The signal generator can also be configured to transmit the output signal to the transducer for production as ultrasound waves. The system can also include a data processing engine configured to be connected to the transducer, the data processing engine configured to receive the digital received signal from the transducer and correlate the digital received signal with the optimized output signal. The system can also include an image generator configured to generate an image based on the correlation of the digital received signal with the optimized output signal. In some embodiments, an ultrasound-based diagnostic medical imaging system can include a display configured to display the generated image to a user.

In some embodiments, the input to the signal generator can be the impulse response function of the transducer convolved with itself. In some embodiments, the optimized output signal can be an Optimal Pulse. In some embodiments, the Optimal Pulse can be calculated with a Gaussian function having a standard deviation between 1 and 3. In some embodiments, the Gaussian function has a standard deviation of 2.5. In some embodiments, the Optimal Pulse can have a threshold value T that is between approximately 0.01% of the maximum absolute value of a Fast Fourier Transform of the input to the signal generator and approximately 10% of the maximum absolute value of the Fast Fourier Transform of the input to the signal generator. In some embodiments, the Optimal Pulse can have a threshold value T that is equal to 0.1% of the maximum absolute value of a Fast Fourier Transform of the input to the signal generator.

In various embodiments, a radar system can include at least one antenna, wherein an impulse response function of the at least one antenna reflects the properties of the antenna and their effect on a signal passing through the antenna; a transmitter configured to be connected to the at least one antenna, the transmitter configured to generate an output signal that is computed from an input that is based on the impulse response function of the at least one antenna, and transmit the output signal through the at least one antenna; a receiver configured to be connected to the at least one antenna, the receiver configured to receive a return signal through the at least one antenna, the receiver further configured to correlate the return signal with the output signal; and an image generator configured to generate an image based on the correlation of the return signal with the output signal. In some embodiments, the radar system can also include a display configured to display the generated image to a user.

In some embodiments, the output signal can be an Optimal Pulse. In some embodiments, the Optimal Pulse can be calculated with a Gaussian function having a standard deviation between 1 and 3. In some embodiments, the Gaussian function has a standard deviation of 2.5. In some embodiments, the Optimal Pulse can have a threshold value T that is between approximately 0.01% of the maximum absolute value of a Fast Fourier Transform of the input to the transmitter and approximately 10% of the maximum absolute value of the Fast Fourier Transform of the input to the transmitter. In some embodiments, the Optimal Pulse can have a threshold value T that is equal to 0.1% of the maximum absolute value of a Fast Fourier Transform of the input to the transmitter.

In some embodiments, a radar system can be a bistatic system such that the at least one antenna includes a first antenna that has a first antenna impulse response function that reflects the properties of the first antenna and their effect on a signal passing through the first antenna, and the at least one antenna also includes a second antenna that has a second antenna impulse response function that reflects the properties of the second antenna and their effect on a signal passing through the second antenna. In some embodiments, the transmitter can be connected to the first antenna and the receiver can be connected to the second antenna. In some embodiments, the input to the transmitter can be the first antenna impulse response function convolved with the second antenna impulse response function.

In some embodiments, a radar system can be a monostatic system such that the transmitter and the receiver are connected to a single antenna that has a single antenna impulse response function that reflects the properties of the single antenna and their effect on a signal passing through the single antenna. In some embodiments, the input to the transmitter can be the single antenna impulse response function convolved with itself.

In various embodiments, a method of producing an optimized pulse for a transducer can include providing a signal generator configured to produce a signal for transmission to a transducer that has an impulse response function, and producing the signal for transmission to the transducer, wherein producing the signal includes the steps of: determining an input that is a function of the impulse response function of the transducer; determining a Fast Fourier Transform of the input; determining the inverse of the Fast Fourier Transform for all values above a threshold value; determining the convolution of the inverse of the Fast Fourier Transform with a Gaussian function; and determining an inverse Fast Fourier Transform of the convolution. The signal can then be transmitted to the transducer.

In some embodiments, the threshold value can be between approximately 0.01% of the maximum absolute value of a Fast Fourier Transform of the input and 10% of the maximum absolute value of a Fast Fourier Transform of the input. In some embodiments, the threshold value can be equal to 0.1% of the maximum absolute value of the Fast Fourier Transform of the input. In some embodiments, the Gaussian function can have a standard deviation between approximately 1 and approximately 3. In some embodiments, the Gaussian function can have a standard deviation of 2.5. In some embodiments, the input can include the impulse response function of the transducer convolved with itself.

DETAILED DESCRIPTION OF THE EMBODIMENTS

Figure 1A:
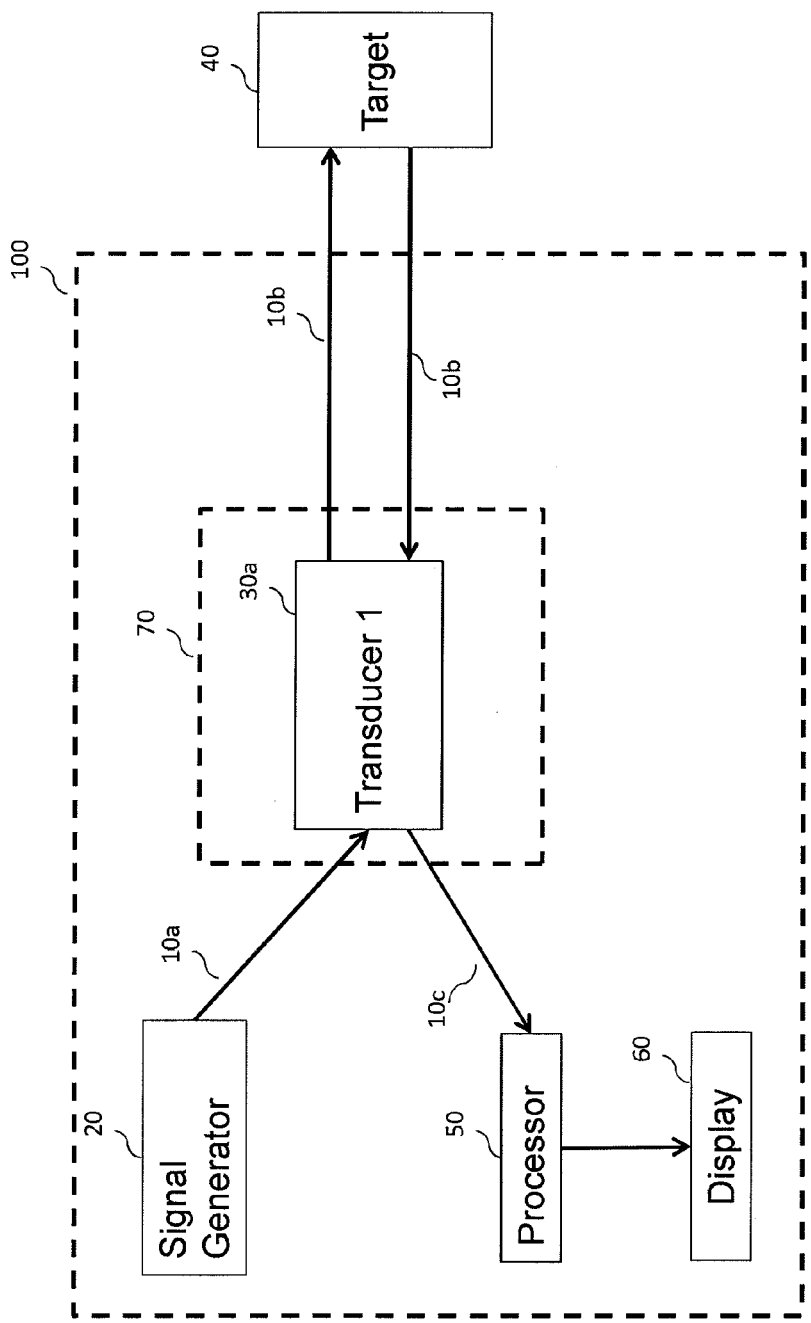
FIG. 1A is a diagram of one embodiment of a pulse compression system.

With reference to the attached figures, certain embodiments and examples of systems and methods for developing improved pulses for a given transducer or system are provided. Various systems and methods for using the improved pulses are also provided. As used herein, the term "transducer" refers to any device that converts a signal from one form of energy to another form of energy. Thus, for example, a transducer could convert an electrical signal into a mechanical signal (for example, an audio or ultrasound signal) or electromagnetic signal. It could also convert mechanical or electromagnetic signals into electrical signals for processing.

One of ordinary skill in the art will appreciate that though the discussion in this disclosure may be provided in the context of transducers used for particular applications, such as ultrasound transducers, the various embodiments described herein can be apply to any type of transducer. For example, the various embodiments herein are readily applicable to RADAR, LIDAR, and SONAR transmitters and receivers, including antenna transmitters and receivers. In some embodiments, systems and methods described herein can be applied to transducers used for Magnetic Resonance Imaging. In some embodiments, systems and methods described herein can be applied to transducers used in computed tomography (CT) or CAT scans. In some embodiments, systems and methods described herein can be used for cell phone transmitters using CDMA, OFDM, or MIMO standards. In some embodiments, systems and methods described herein can be used with television antennas, optical interferometers, or other applications.

In some of the embodiments disclosed herein, an impulse response function of a transducer(s) can be used by a pulse generator to generate an optimal pulse for use in a pulse compression system in order to create improved range and/or improved spatial resolution and/or quality of images generated with the system. In some embodiments, the optimal pulse can be configured to account for the impulse response of the transducer in such a way to reduce and/or eliminate the modification of a desired input signal from its intended form. Further, the optimal pulse can be configured such that, after the optimal pulse is inputted into a transducer and is affected by the impulse response function of the transducer, the resulting signal comprises the desired signal form or is closer to the desired signal form than otherwise would result if a non-optimized pulse were used.

In an embodiment, the system comprises a transducer that is configured to transmit and receive signals from a target. In such an embodiment, the system can be configured to generate the optimal pulse by accessing the impulse response function of the transducer and convolving the impulse response function with itself. The system can be configured to take a Fourier transform of the resulting function. The system can be configured to define the threshold T as a function of the Fourier transform. The system can be configured to take the inverse of the Fourier transform where the Fourier transform is greater than the threshold T to produce a first function. The system can be configured to take the inverse Fourier transform of the first function to generate a second function. The system can be configured to multiply the second function by a Gaussian function in order to generate an optimal pulse function that is configured to produce an optimal pulse for the particular transducer.

In an embodiment, the system comprises a first transducer that is configured to transmit signals to a target and a second transducer that is configured to receive signals from the target. In such an embodiment, the system can be configured to generate the optimal pulse by accessing the impulse response functions of the first transducer and the second transducer, and convolving the impulse response functions with each other. The system can be configured to take a Fourier transform of the resulting function. The system can be configured to define the threshold T as a function of the Fourier transform. The system can be configured to take the inverse of the Fourier transform where the Fourier transform is greater than the threshold T to produce a first function. The system can be configured to take inverse Fourier transform of the first function to generate a second function. The system can be configured to multiply the second function by a Gaussian function in order to generate an optimal pulse function that is configured to produce an optimal pulse for the particular transducer.

Generally, a signal transmission system, an imaging system, or other pulse compression systems include a signal generator that generates a desired signal that is passed through a transducer and/or other components of the system. The transducer and/or other components can have an electromechanical impulse response that will affect the signal, modifying it from its original, desired form. These modifications can adversely impact the resolution, range, and/or other characteristics of the system. Various embodiments described herein relate to methods and systems for designing an optimal pulse best suited for any given transducer or combination of transducers and/or other components. An optimal pulse can account for the properties of these various components and the effect that they have on a signal.

For example, in the context of ultrasound medical imaging, a transducer can be utilized to generate medical images to enable a physician to make a medical diagnosis of a patient. Typically, an ultrasound imaging system can be configured to generate a digital signal that is inputted into a transducer. The transducer can be configured to convert the digital signal into an analog signal. The transducer can be configured to transmit the analog signal into a body portion of the patient, for example the abdomen of the patient, that the physician desires to be imaged. A portion of the analog signal is configured to penetrate through the body of the patient while a second portion of the analog signal is configured to be reflected off various tissues in the body. The transducer can be configured to receive reflected analog signals. The transducer can be configured to convert the reflected analog signals into digital signals. The imaging system can be configured to process the digital signals generated from the reflected analog signals from the patient in order to generate an electronic medical image of the body portion of the patient.

In some instances, the electronic medical image that is generated by the imaging system can be less than clear and/or contain artifacts and/or be of poor quality. Poor image clarity and/or artifacts can be the result of alterations made to the original digital signal when the digital signal is converted into an analog signal by the transducer. For example, an ultrasound transducer can comprise a piezoelectric crystal that can be utilized to convert a digital signal into an analog ultrasound signal. During this conversion process, the ultrasound transducer can in some instances modify the original signal based on characteristics of the ultrasound transducer. These modifications to the original signal can add noise to the signal. Such signal noise can remain in the reflected analog signal that is received back from the body of the patient by the ultrasound transducer. The ultrasound transducer can be configured to convert the reflected analog signal with the noise into a digital signal for processing by the imaging system. During this conversion process, the ultrasound transducer may introduce still more noise into the reflected analog signal. Also, the bandwidth of the transducer may significantly alter the frequency characteristics of the original signal.

In some instances, the noise introduced from the first conversion and/or the second conversion can interfere with the signal processing performed by the imaging system and/or cause the imaging system to produce a poor quality medical image that may contain artifacts.

In some embodiments, the systems and methods disclosed herein are configured to generate a digital signal that is configured to account for the conversion characteristics of a transducer. For example, the system can be configured to access an impulse response function that is representative of the characteristics of the transducer. The system can be configured to utilize the function in order to generate an original signal that can account for and/or cancel the noise that is introduced by the transducer when the transducer converts the original digital signal into an analog signal. In an embodiment, the system can be configured to utilize the impulse response function in order to generate an original signal that can account for and/or cancel the noise that is introduced by the transducer when the transducer converts the reflected analog signal into a digital signal for processing by the imaging system. Also, the system can be configured to generate an original signal such that the pulse that emanates from the transducer can have a constant frequency response (or as close to a constant frequency response as possible) throughout the range of frequencies within the bandwidth of the transducer. In various embodiments, the principles described in this and the above paragraphs can also be applied outside of the context of ultrasound medical imaging, such as in RADAR, LIDAR, SONAR, or other applications discussed herein.

FIG. 1A illustrates one embodiment of a pulse compression system 100. As illustrated, in some embodiments the system can include a pulse or signal generator 20 that generates a digital signal or pulse 10a. The signal 10a can be passed to an operations module 70, which can transform the signal 10a from an electrical signal to a signal 10b (for example, an electromagnetic or mechanical signal) that can be directed toward a target 40. In some embodiments, as illustrated, the operations module 70 can comprise a transducer 30a, and the signal 10a can pass through the transducer. On passing through the transducer, the signal is modified according to the impulse response of the transducer, as discussed above, such that the signal 10b is not equivalent to the signal 10a.

The signal 10b can be reflected from the target 40 and accessed by the operations module 70, and the transducer 30a can convert it to an electronic or digital signal that is conveyed to a processor 50. The processor can be used to correlate the received signal with the generated signal to create an image of the target that can be shown on a display 60. However, the signal 10c that enters the processor is modified again by the impulse response of the transducer 30a through which it passes after reflection from the target, such that the signal 10c differs further from the signal 10a. These differences can negatively impact an image produced from the correlation of the received signal with the generated signal.

Figure 1B:
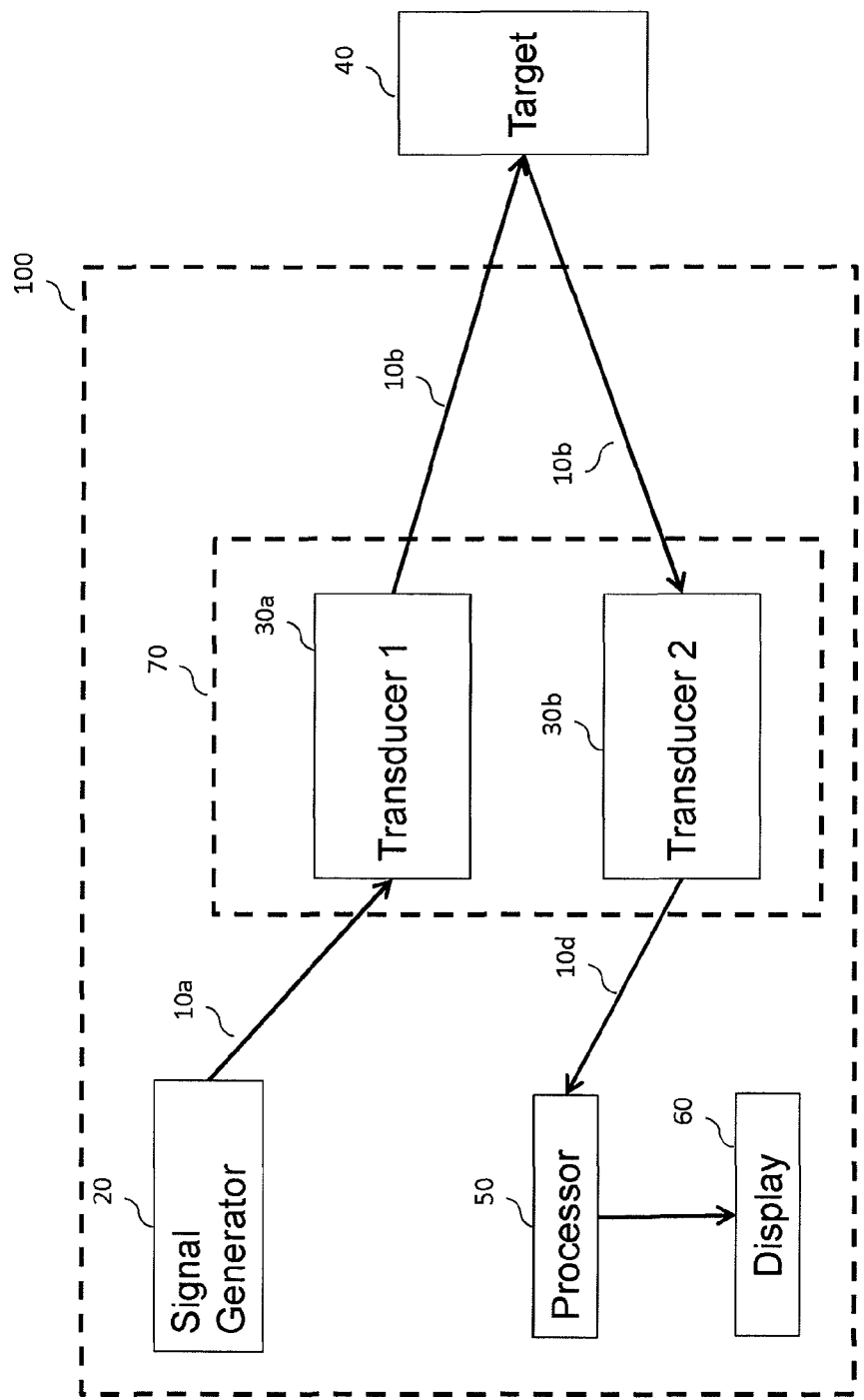
FIG. 1B is a diagram of one embodiment of a pulse compression system.

In some embodiments, as illustrated in FIG. 1B, a pulse compression system 100 can include an operations module 70 that has a plurality of transducers, such as a first transducer 30a and a second transducer 30b. The signal 10a generated by the signal generator 20 can be passed to the first transducer 30a, which converts the signal into a form for transmission to the target, as described above. A reflected signal can be received by the second transducer 30b, which can convert the signal into an electric or digital signal that is passed to the processor 50. Also as above, the signal processor can correlate the received signal with the generated signal to create an image of the target. In this case, the received signal has been modified from the original generated signal 10a by the impulse responses of the second transducer 30b and the first transducer 30a.

Figure 2A:
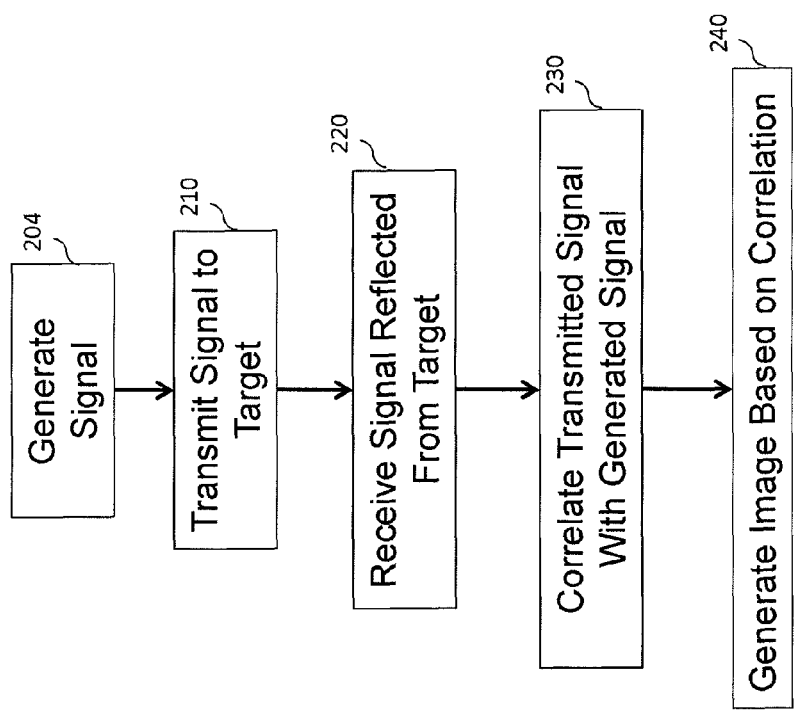
FIG. 2A is a flow chart of one embodiment of a method of using a pulse compression system disclosed herein.
Figure 2B:
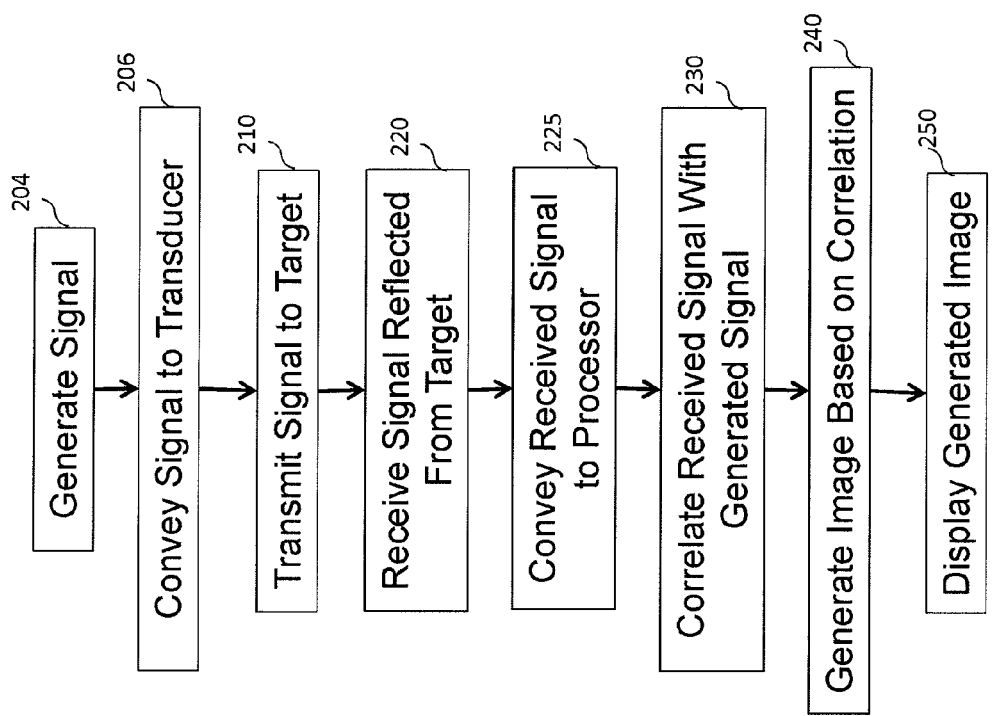
FIG. 2B is a flow chart of one embodiment of a method of using a pulse compression system disclosed herein.

FIGS. 2A and 2B illustrate flow diagrams of embodiments of this process. As illustrated in FIG. 2A, operating a pulse compression system can begin with generating a signal, illustrated at block 204. At block 210, the signal is transmitted to a target. At block 220, the system receives a signal reflected from the target. At block 230, the transmitted signal and generated signal are correlated, and at block 240 an image is generated based on that correlation.

FIG. 2B illustrates a more detailed flow diagram of one embodiment. As illustrated in the embodiment of FIG. 2B, from the signal generation block 204 the signal is conveyed or transmitted to a transducer at block 206. The transducer can transmit the signal toward a target at block 210. At block 220, a reflected portion of the signal is accessed by the pulse compression system. As described above, the signal can be accessed by the transducer that transmitted the signal or it can be accessed by a different transducer. At block 225, the signal is conveyed to a processor. At 230, the processor correlates the received signal with the generated signal, and at block 240 an image can be generated based on the correlation. At block 250, that image can be provided on a display.

Figure 2C:
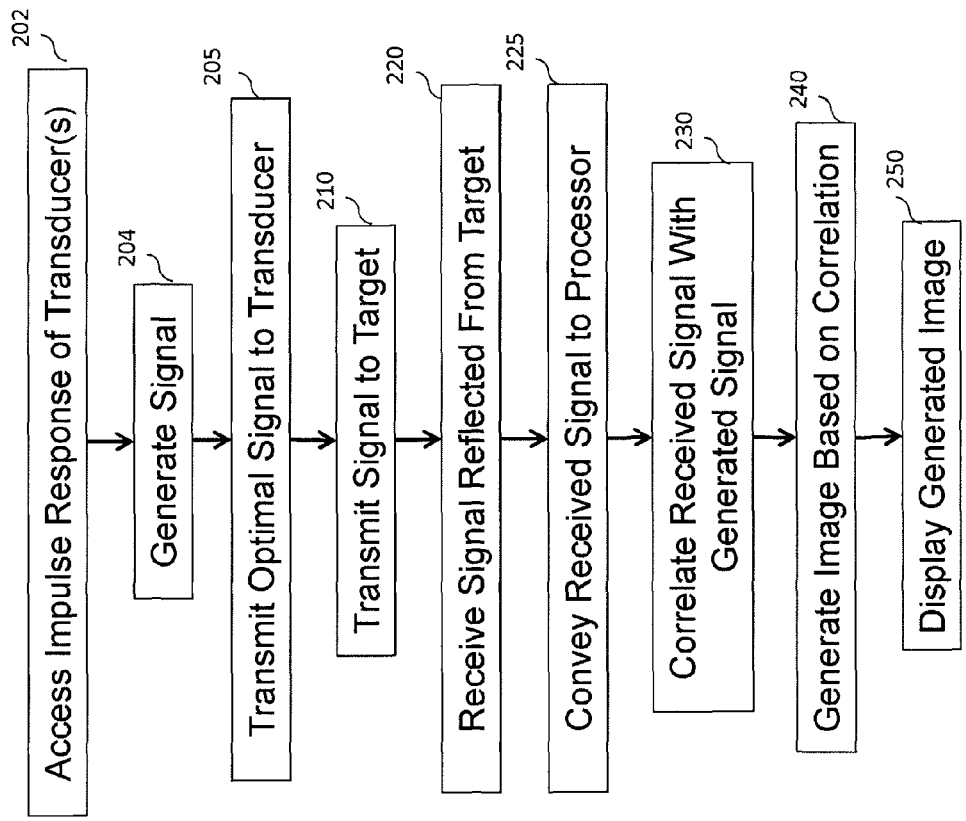
FIG. 2C is a flow chart of one embodiment of a method of using a pulse compression system disclosed herein.

Similar to FIG. 2B, FIG. 2C illustrates a more detailed flow diagram of embodiments of the pulse compression systems disclosed herein. At block 202, the system can be configured to access an impulse response function of the transducer. At block 204, the system can be configured to generate an optimal pulse signal. In an embodiment, the optimal pulse signal is generated based on the impulse response function of the transducer. In an embodiment, the system utilizes the impulse response function of the transducer to generate an optimal pulse signal that is configured to account for modifications introduced by the transducer when a signal is inputted into and is converted by the transducer. At block 206, the system can be configured to transmit the optimal pulse signal to the transducer. In an embodiment, the transducer can be configured to convert the optimal pulse signal into an analog signal for transmission into a target. At block 210, the system can be configured to transmit the signal produced by the transducer to the target. In an embodiment, at block 220, the system and/or the transducer can be configured to receive reflected signals from the target. In an embodiment, the system and/or the transducer can be configured to convert the received reflected signals from the target into a digital signal. A block 225, the system can be configured to transmit the digital signal of the received reflected signals to a processor for processing. At block 230, the system can be configured to correlate the digital signal of the received reflected signals with the generated optimal pulse signal. At block 240, the system can be configured to generate an image based on the correlation. At block 250, the system can be configured to display the generated image.

Various embodiments described herein related to systems and methods of generating an initial signal 10a in view of expected modifications to the signal from the transducer(s), such that the signal ultimately emitted, received, and correlated can be used to produce improved range and resolution of imaging and transmission systems.

Figure 3:
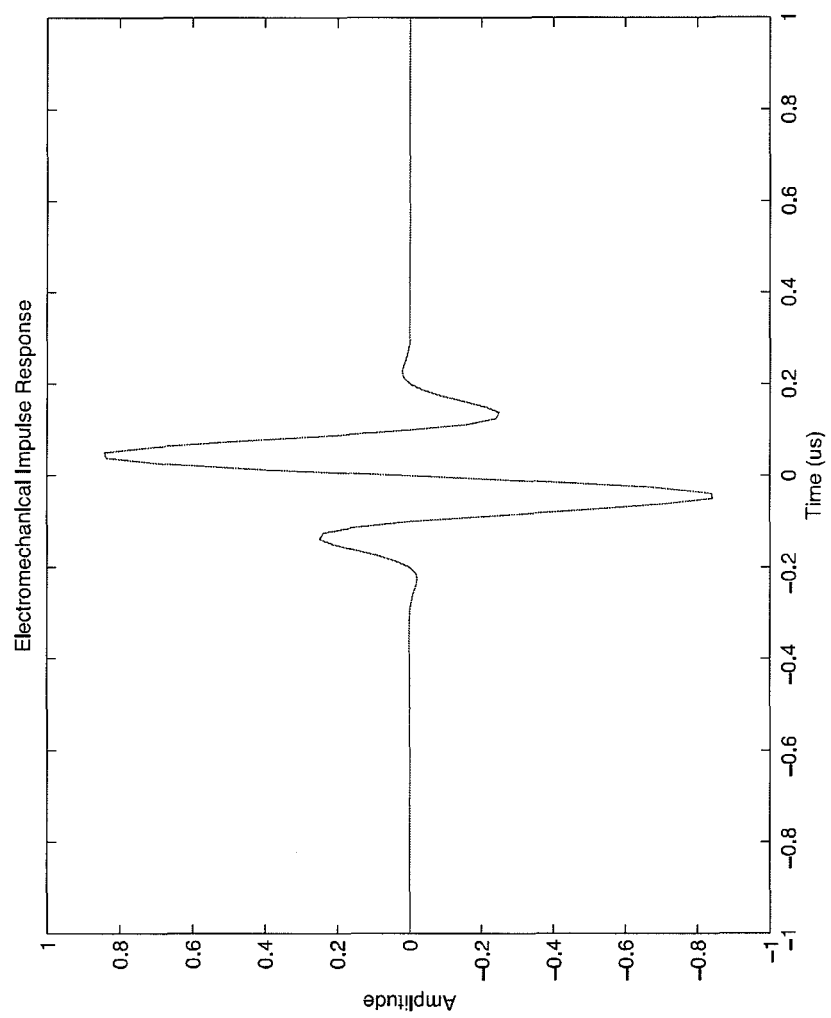
FIG. 3 is a chart illustrating the impulse response of a transducer.

Different transducers can have different impulse responses. FIG. 3 illustrates one embodiment of the impulse response of a first transducer with a 5 MHz center frequency for use in medical ultrasound. An ideal transducer has the Dirac delta function as its impulse response, though transducers can typically have an impulse response similar to that illustrated in FIG. 3.

Preferably, a pulse generated for a pulse compression system can be configured such that auto correlation of the convolution of the generated pulse with the impulse responses of the transducers in the pulse compression system results in a function as close to the delta function as possible. In other words, a perfectly optimized input pulse sopt(n) will satisfy the following equation:

$$sopt(n)°h(n)=\delta(0) \quad (3)$$

where ° denotes the convolution operator, h(n) denotes a function of the transducer impulse response, and δ(0) is a single impulse. Equation 4, below, represents a mathematical definition of a convolution of an optimal pulse function and a transducer impulse response function operating in the continuous time domain (t), where τ represents a shift in the transducer impulse response function.

$$\int sopt(t)h(t-\tau)dt=\delta(0) \quad (4)$$

In some embodiments, a method of producing an optimized pulse can include defining an input as a function of the impulse response of the transducer(s) in a pulse compression system and computing the transfer function (for example, computing the Fast Fourier Transform (FFT)) of the input. The inverse of that result can be computed, and then an inverse FFT (IFFT) can be computed. That result can be multiplied with a Gaussian function to produce an optimal pulse. This process can be performed by a computing system, various embodiments of which are described in more detail below with respect to FIG. 24. One embodiment of a method of producing an optimized pulse can include the following:

1) Define an input h(n) that is a function of the impulse responses of one or more transducers.
2) Compute H(f) as the FFT of h(n).
3) Define a threshold T=0.001*max(abs(H(f)))
4) Define Hinv(f) as:
   If (H(f)>T) Hinv(f)=1/H(f);
   else Hinv(f)=0;
5) The optimal pulse sopt(n)=IFFT(Hinv(f))*g(t), where g(t) is a Gaussian function with a standard deviation of 2.5.

In various embodiments, the input h(n) can have different forms. Preferably, the input h(n) can be designed to reflect the particular system in use and can provide a measure of the total impulse response of the system. For example, in a system such as that illustrated in FIG. 1, where the first transducer 30a emits and receives the signal, and where the first transducer 30a has an impulse response $h_1(n)$, the input h(n) can be defined as $h_1(n)°h_1(n)$, where ° denotes the convolution operator. Convolving the impulse response $h_1(n)$ with itself accounts for the fact that the signal passes through the transducer twice—once while being emitted and once while being received. In some embodiments, where a first transducer having an impulse response $h_1(n)$ is used to transmit the signal and a second transducer having an impulse response $h_2(n)$ is used to receive the signal, the input h(n) can be defined as $h_1(n)°h_2(n)$. In some embodiments, $h_1(n)$ can be approximately equal to $h_2(n)$. In some embodiments, where additional aspects of a system have an impulse response and affect a signal passing through the system, those aspects can be incorporated into the input h(n). Thus, in some embodiments the input h(n) can be defined as $h_1(n)°h_2(n)°h_3(n) \ldots °h_n(n)$. In some embodiments, the input h(n) can be the single impulse response $h_1(n)$ of a transducer.

In various embodiments, different values can be used to adjust the optimal pulse. For example, in some embodiments the threshold T can be set at any value between approximately 0.0001*max(abs(H(f))) and approximately 0.1*max(abs(H(f))). In some embodiments, it can be greater than approximately 0.1*max(abs(H(f))). In some embodiments, it can be less than approximately 0.0001*max(abs(H(f))).

In some embodiments, the Gaussian function g(t) that is used can have a standard deviation that differs from 2.5. For example, in some embodiments the Gaussian function can have a standard deviation between approximately 1 and approximately 3. In some embodiments, the Gaussian function used can have a standard deviation that is less than 1. In some embodiments, the Gaussian function used can have a standard deviation that is greater than 3.

A generalized embodiment of a method of determining an optimized input pulse for a given transducer impulse response can include:

1) Define an input h(n) that is a function of the impulse response(s) of the transducer(s) in a pulse compression system.
2) Compute H(f) as the FFT of h(n).
3) Define a threshold value T as a function of the maximum absolute value of H(f).
4) Define Hinv(f) as:

If (H(f)>T) HInv(f)=1/H(f);
else Hinv(f)=0;
5) The optimal pulse sopt(n)=IFFT(Hinv(f))*g(t), where g(t) is a Gaussian function.

References in the specification and/or claims to an Optimal Pulse refer to the optimal pulse sopt(n) computed through this general embodiment. As above, this method can be performed by a computing system, various embodiments of which are described in more detail below with respect to FIG. 24.

Figure 4:
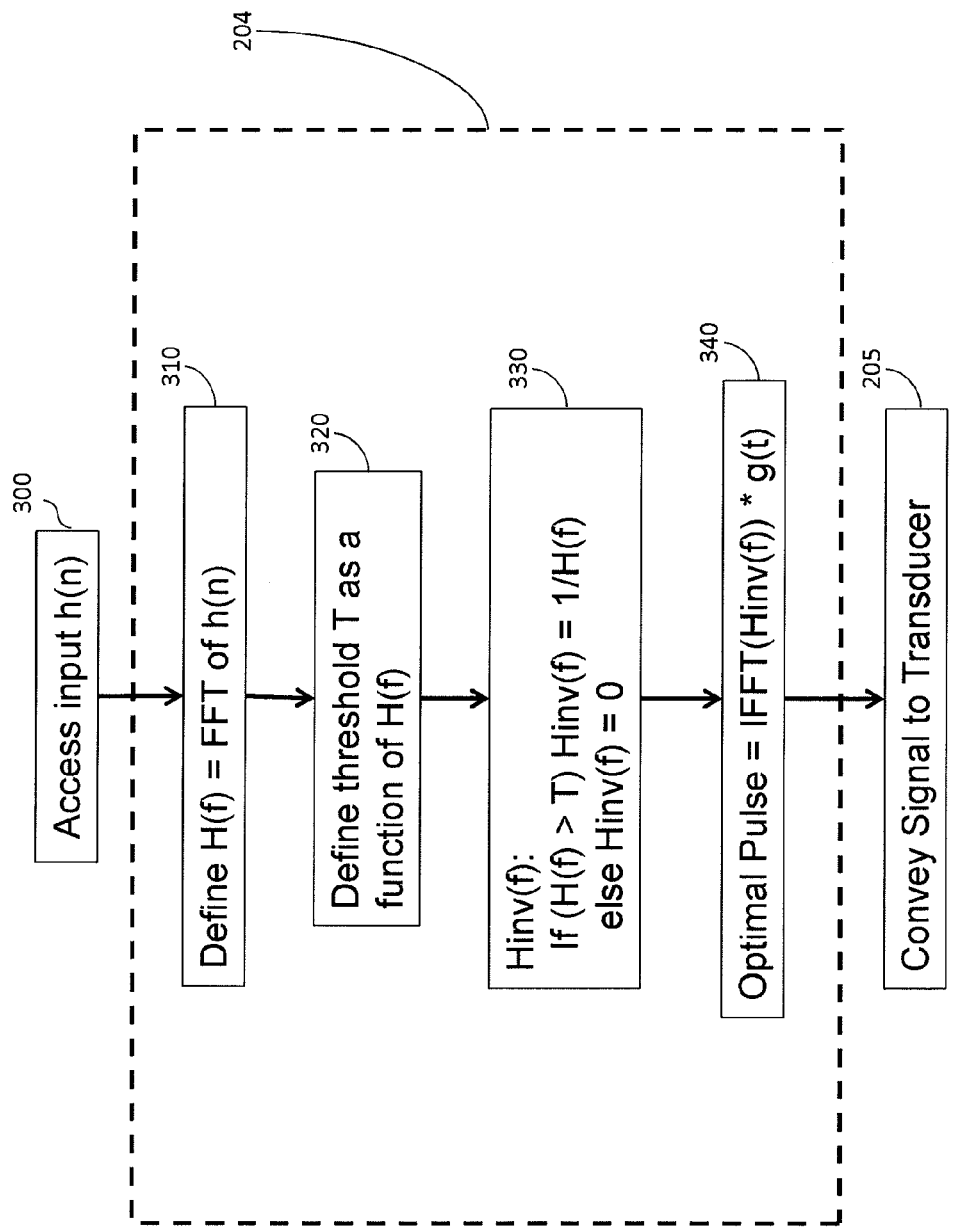
FIG. 4 is a flow chart of one embodiment of a method of generating an optimal pulse.

FIG. 4 illustrates a flow chart of one embodiment of a method of generating an optimized pulse for use within a pulse compression system. For example, as illustrated, the method can be performed within a signal generation block 204, such as the signal generation block 204 of FIG. 2B. At block 300 an input to the signal generation block 204 is accessed. As described, the input can be a function of the impulse response(s) of the transducer(s) of the pulse compression system. Also as described, the signal generation block 204 can include defining H(f) (block 310); defining a threshold value (block 320); defining Hinv(f) (block 330); and determining an optimal pulse as IFFT(Hinv(f))*g(t) (block 340). At block 206, that optimal pulse can then be conveyed to a transducer.

Figure 5A:
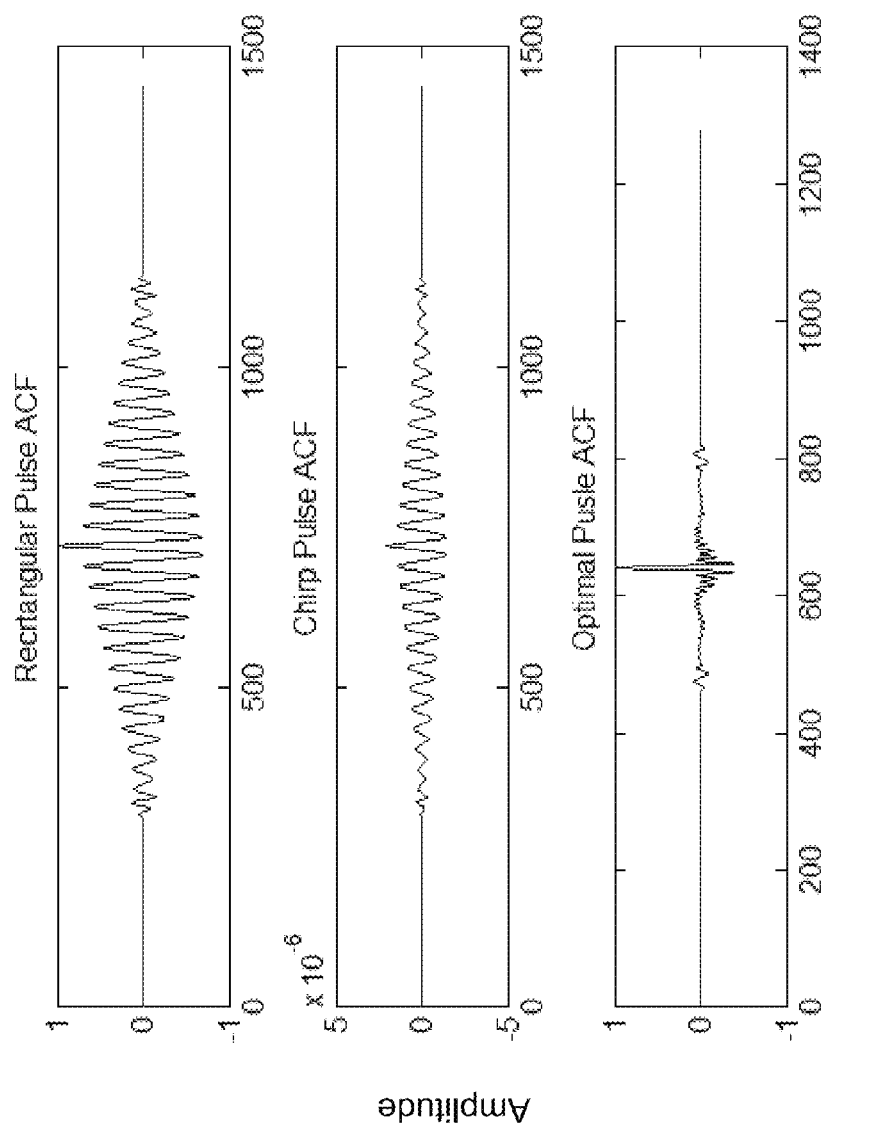
FIG. 5A is a chart illustrating the autocorrelation functions of a rectangular pulse, a chirp pulse, and one embodiment of an optimized pulse for a first transducer.
Figure 5B:
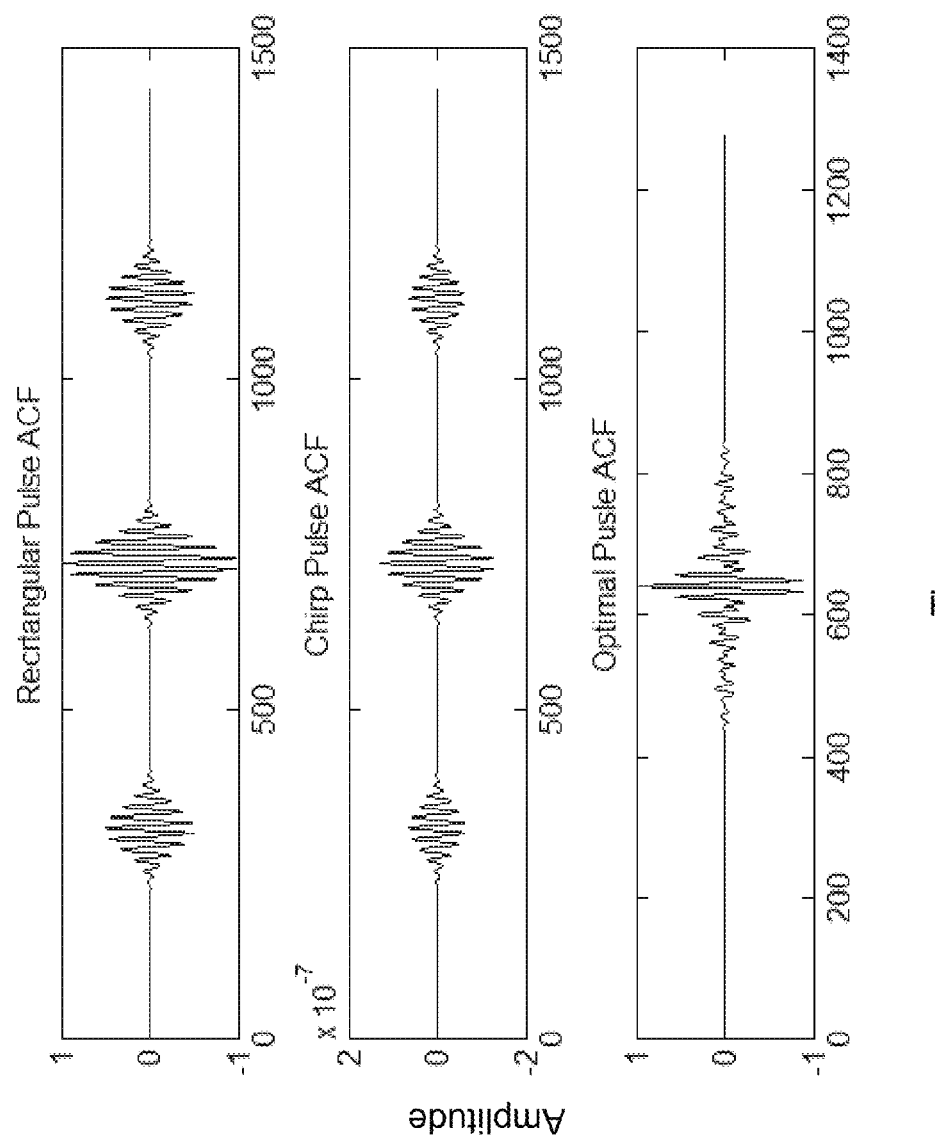
FIG. 5B is a chart illustrating the autocorrelation functions of a rectangular pulse, a chirp pulse, and one embodiment of an optimized pulse for a second transducer.
Figure 5C:
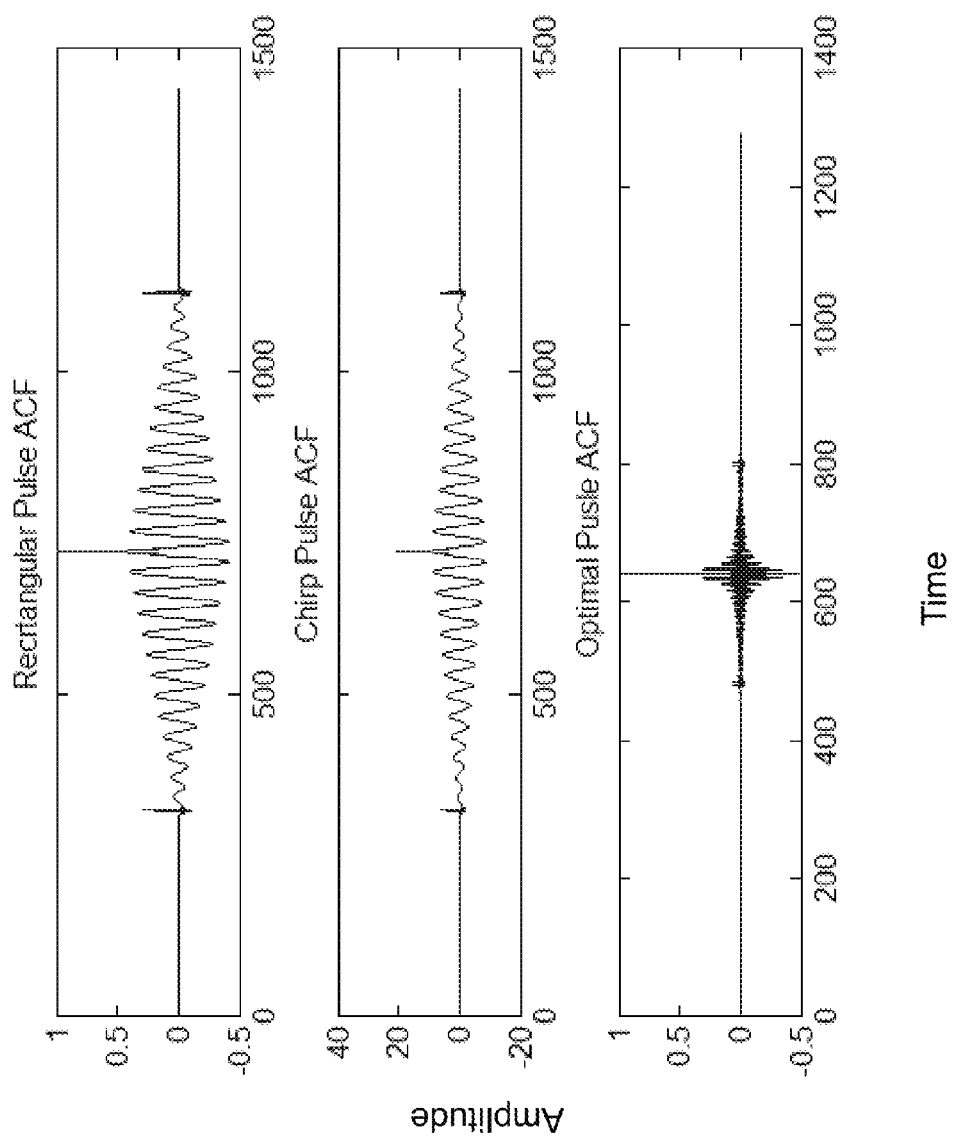
FIG. 5C is a chart illustrating the autocorrelation functions of a rectangular pulse, a chirp pulse, and one embodiment of an optimized pulse for a third transducer.

FIGS. 5A through 5C illustrate autocorrelation functions for each of a rectangular pulse, a chirp pulse, and an optimal pulse determined as described above. FIG. 5A illustrates the autocorrelation function for each pulse when used with the first transducer, the impulse response of which is illustrated in FIG. 3, as described above. FIG. 5B illustrates the autocorrelation function for each pulse when used with a second transducer that has half the bandwidth of the first transducer. FIG. 5C illustrates the autocorrelation function for each pulse when used with a third transducer that has ten times the bandwidth of the first transducer. The input h(n) used for determining the optimal pulse used to produce FIGS. 5A through 5C was the impulse response $h_1(n)$ of the respective transducer convolved with itself. The optimal pulse was also calculated with a threshold of 0.001*max(abs(H(f))) and a Gaussian function having a standard deviation of 2.5.

As illustrated, the autocorrelation functions of the optimal pulse approximate a delta function much more closely than the other pulses. Additionally, as illustrated by a comparison of FIGS. 5A through 5C, the optimal pulse yields an improved autocorrelation function for transducers of varying bandwidth. Further, and as illustrated, the optimal pulse can be effectively used with both narrowband and wideband transducers.

Figure 6:
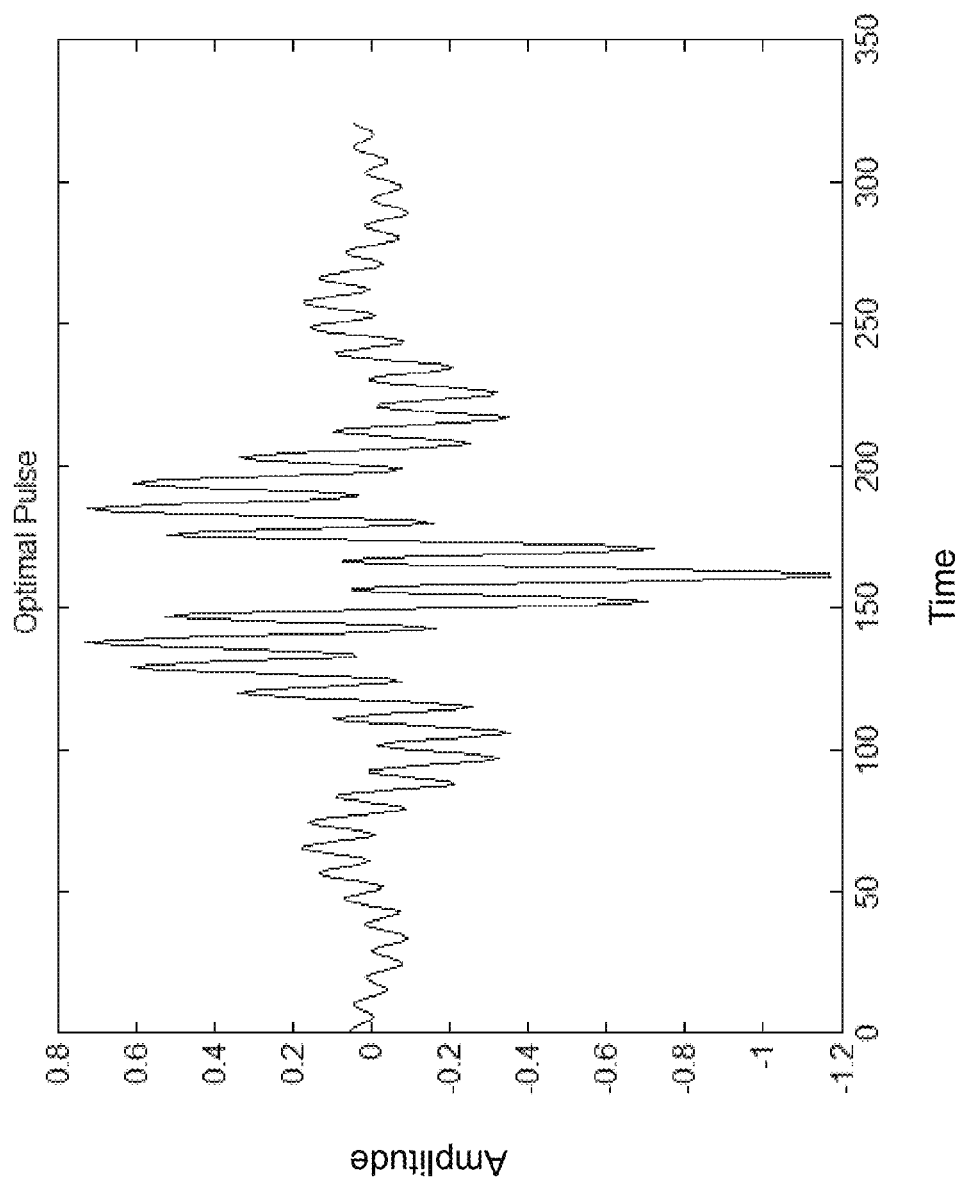
FIG. 6 is a chart showing an optimized pulse for the first transducer.
Figure 7:
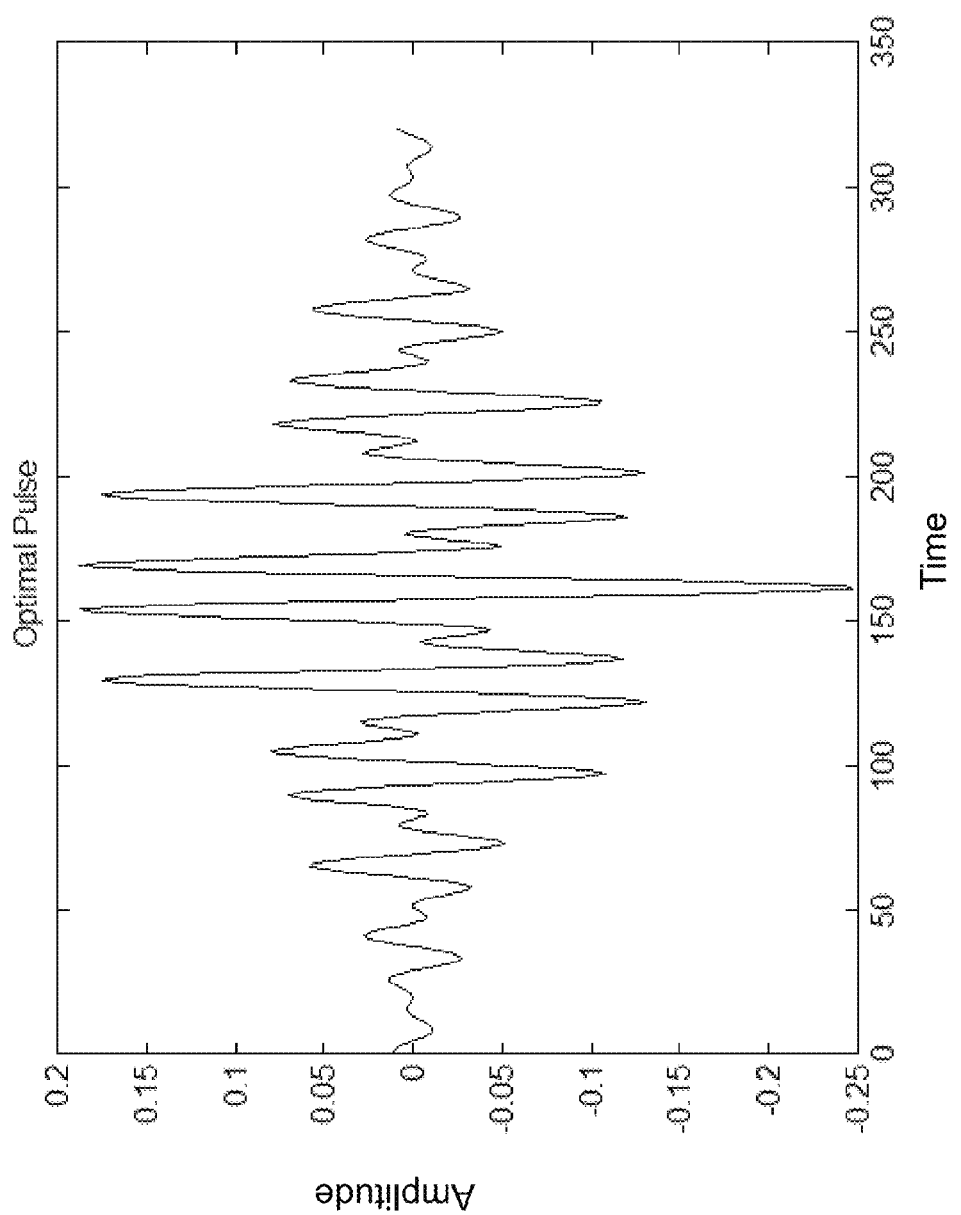
FIG. 7 is a chart showing an optimized pulse for the second transducer.
Figure 8:
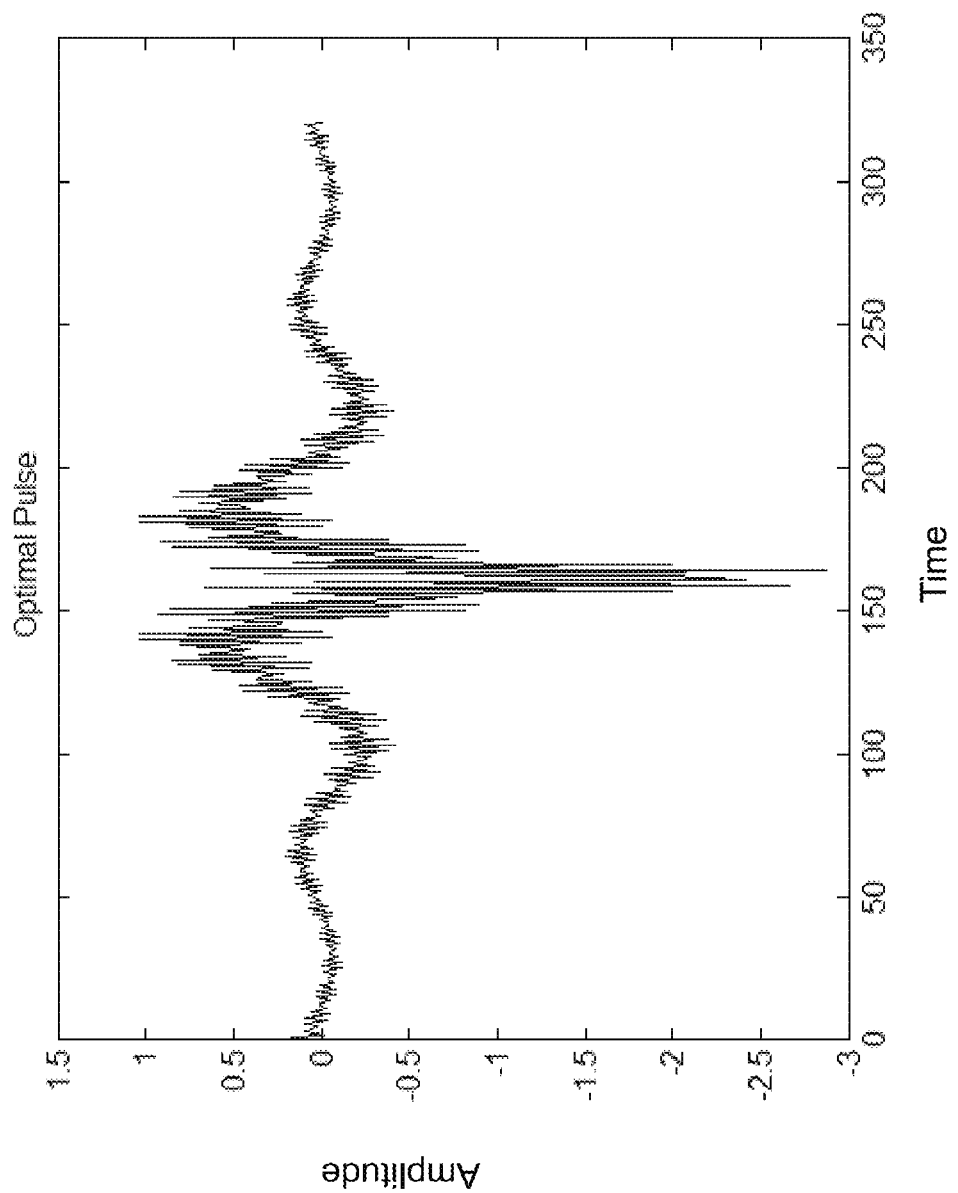
FIG. 8 is a chart showing an optimized pulse for the third transducer.

FIGS. 6 through 8 illustrate the optimal pulses that were generated for each of the three transducers. FIG. 6 illustrates the optimal pulse used for the first transducer. FIG. 7 illustrates the optimal pulse used for the second transducer. FIG. 8 illustrates the optimal pulse used for the third transducer.

Figure 9:
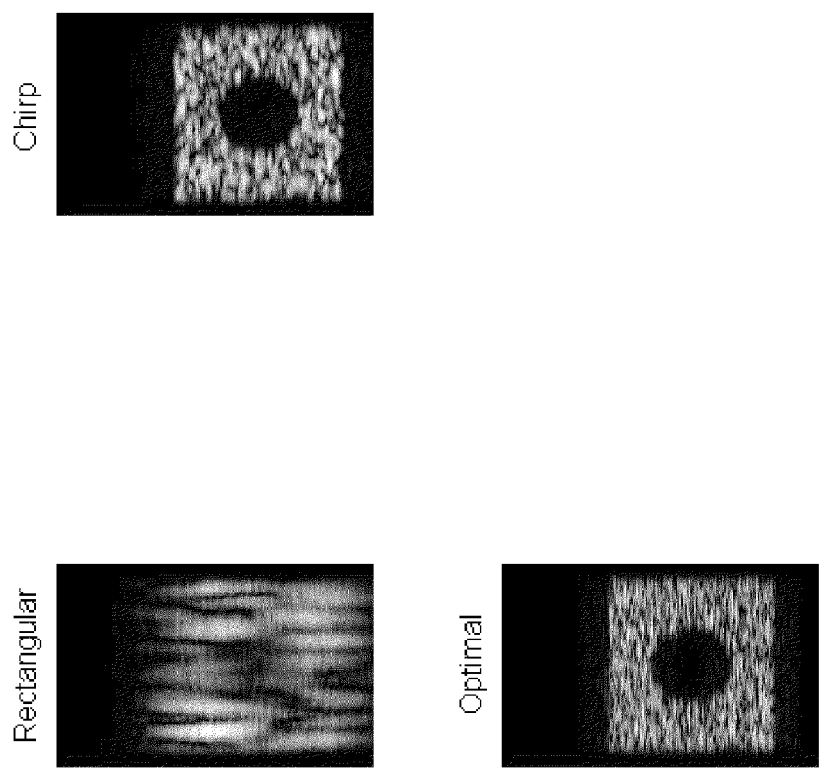
FIG. 9 illustrates ultrasound images with simulated lateral blurring for the rectangular, chirp, and optimal pulses with the first transducer.
Figure 10:
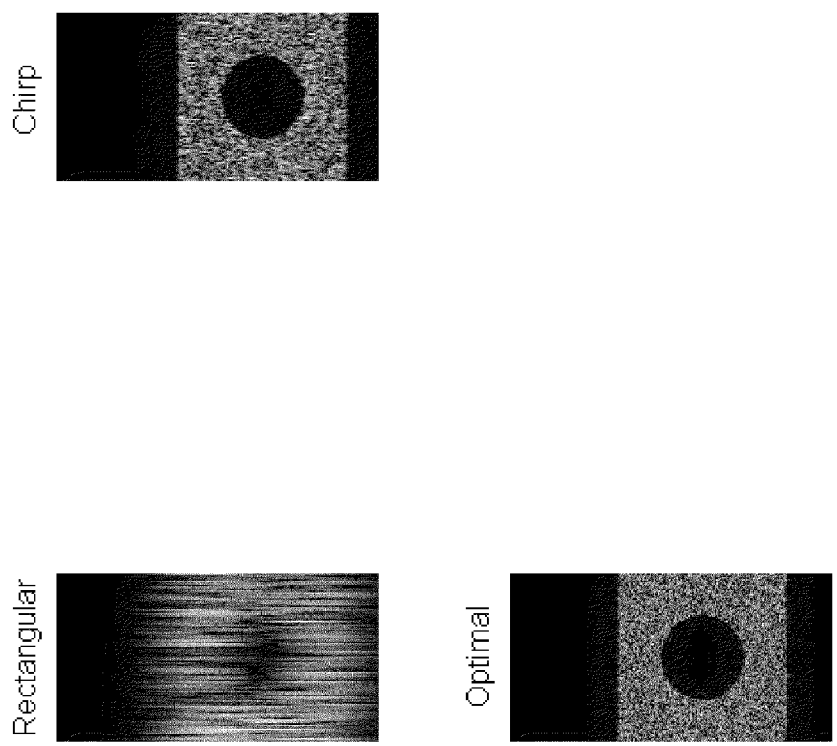
FIG. 10 illustrates ultrasound images for the rectangular, chirp, and optimal pulses with the first transducer.
Figure 11:
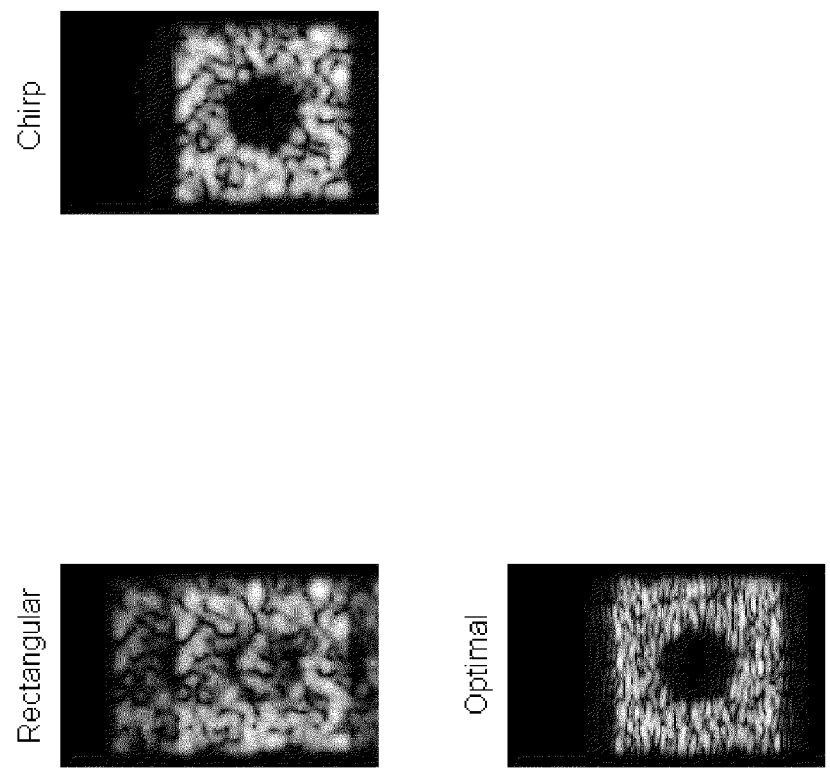
FIG. 11 illustrates ultrasound images with simulated lateral blurring for the rectangular, chirp, and optimal pulses with the second transducer.
Figure 12:
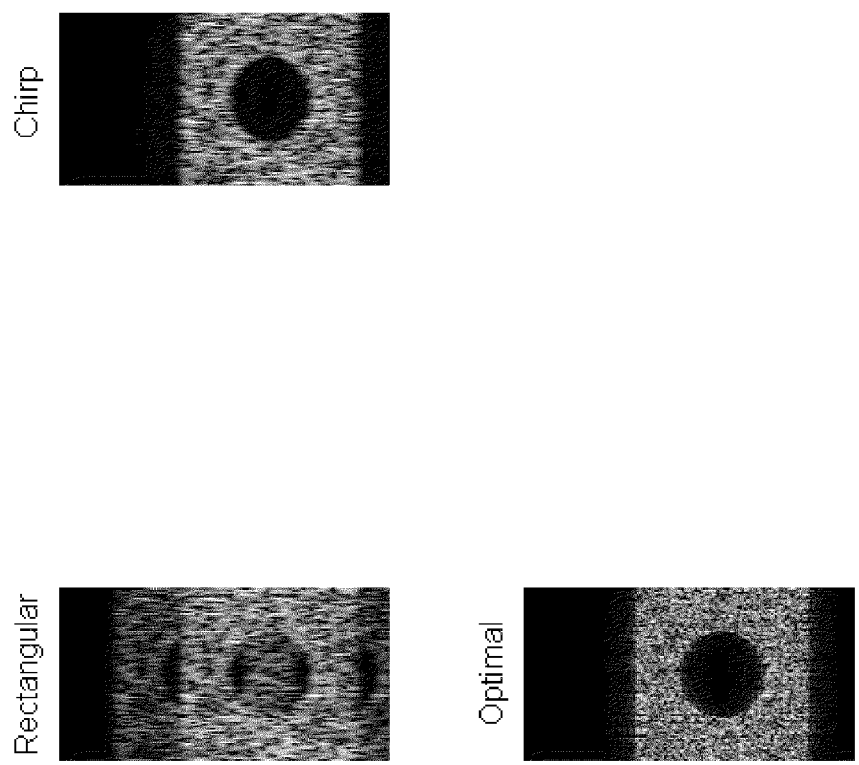
FIG. 12 illustrates ultrasound images for the rectangular, chirp, and optimal pulses with the second transducer.
Figure 13:
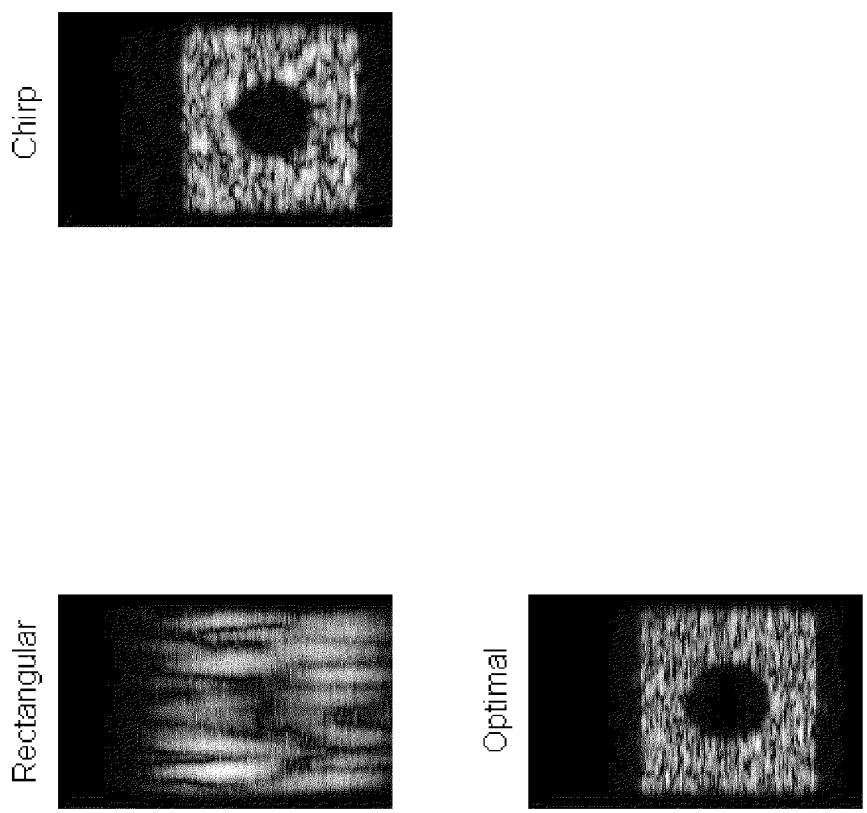
FIG. 13 illustrates ultrasound images with simulated lateral blurring for the rectangular, chirp, and optimal pulses with the third transducer.
Figure 14:
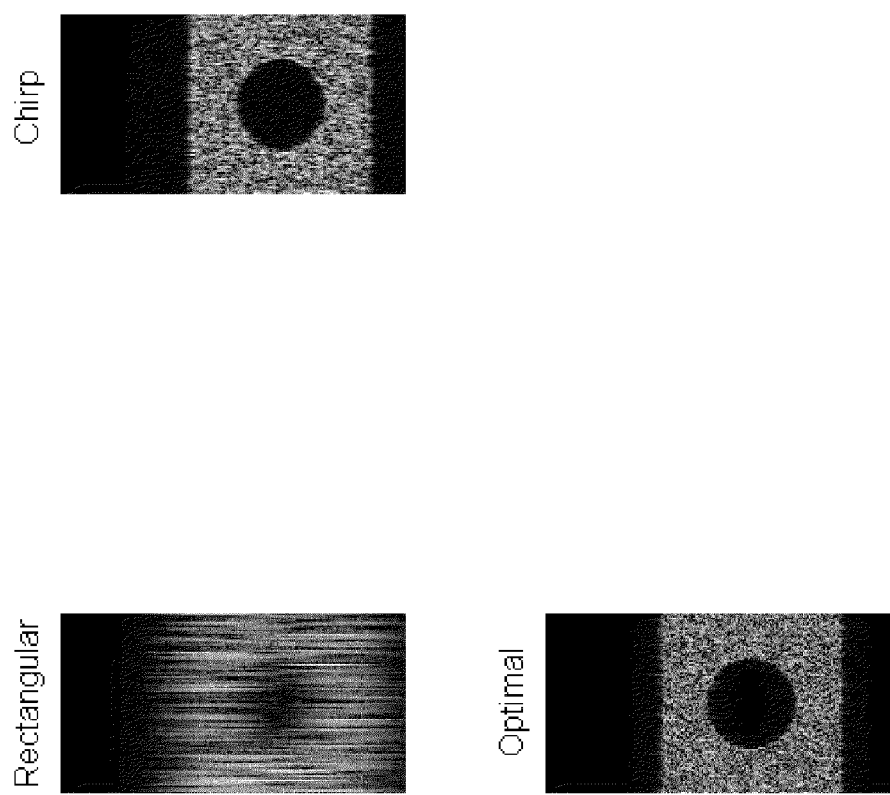
FIG. 14 illustrates ultrasound images for the rectangular, chirp, and optimal pulses with the third transducer.

FIGS. 9 through 14 illustrate results from software simulations of ultrasound images produced using different pulse signals with the first, second, and third transducers. Thus, for example, FIG. 9 illustrates ultrasound images for the rectangular, chirp, and optimal pulses with the first transducer. FIG. 9 includes simulated lateral blurring that is frequently found in medical ultrasound images. FIG. 10 illustrates ultrasound images for the rectangular, chirp, and optimal pulses with the first transducer, but without simulated lateral blurring. In many applications, such as RADAR, the lateral blurring is not that significant. FIG. 11 illustrates ultrasound images for the rectangular, chirp, and optimal pulses with the second transducer with simulated lateral blurring. FIG. 12 illustrates ultrasound images for the rectangular, chirp, and optimal pulses with the second transducer without simulated lateral blurring. FIG. 13 illustrates ultrasound images for the rectangular, chirp, and optimal pulses with the third transducer with simulated lateral blurring. FIG. 14 illustrates ultrasound images for the rectangular, chirp, and optimal pulses with the third transducer without simulated lateral blurring. As can be seen in these figures, the images generated with the optimal pulse are consistently clearer and produce a superior range resolution image than those generated with alternate input pulses.

The ambiguity function, which depends on the time delay and Doppler frequency of a signal, can reflect the distortion of a returned pulse and consequently provide an indication of the effectiveness of a pulse for radar and other applications. The ambiguity function can be defined as:

$$\chi(\tau,f)=\int_{-\infty}^{\infty}s(t)s^*(t-\tau)e^{i2\pi ft}dt \quad (5)$$

where f reflects the Doppler frequency and $\tau$ reflects the time delay.

Figure 15:
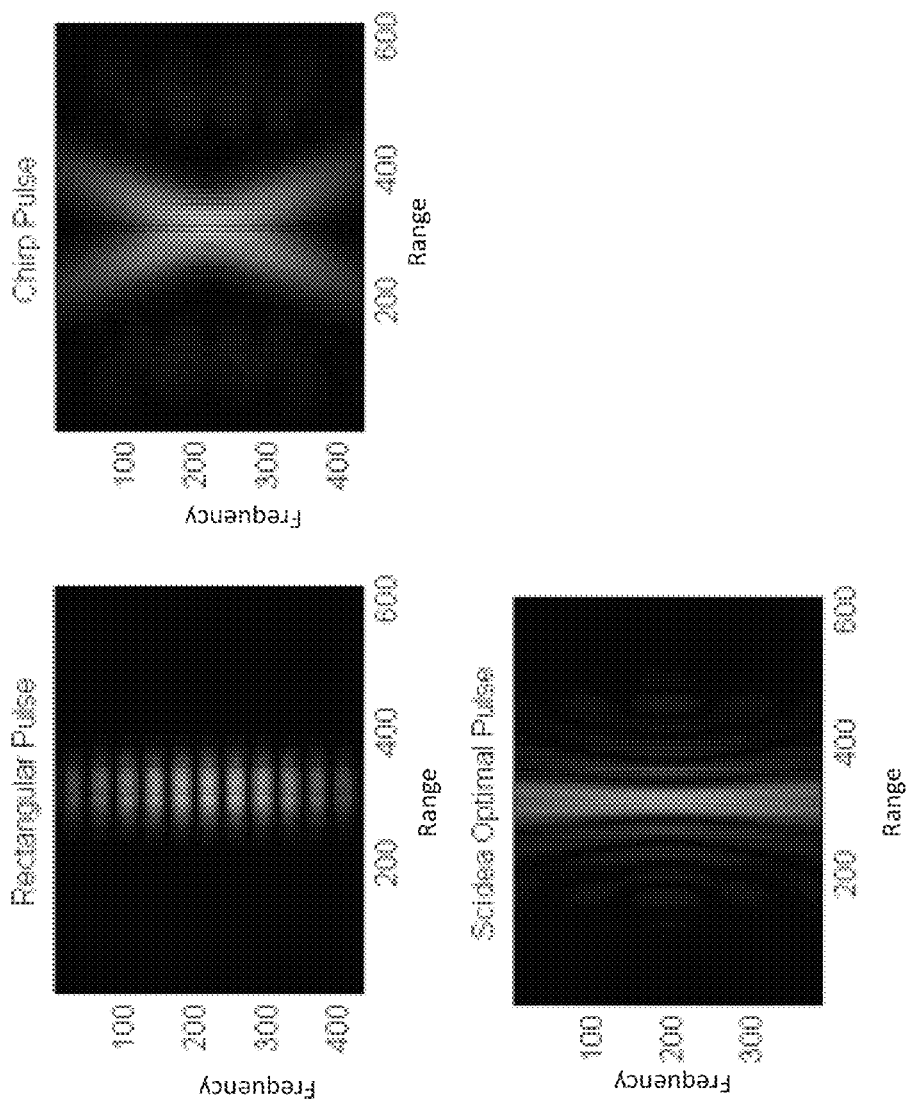
FIG. 15 illustrates plots of the ambiguity functions for the rectangular, chirp, and optimal pulses with the first transducer.
Figure 16:
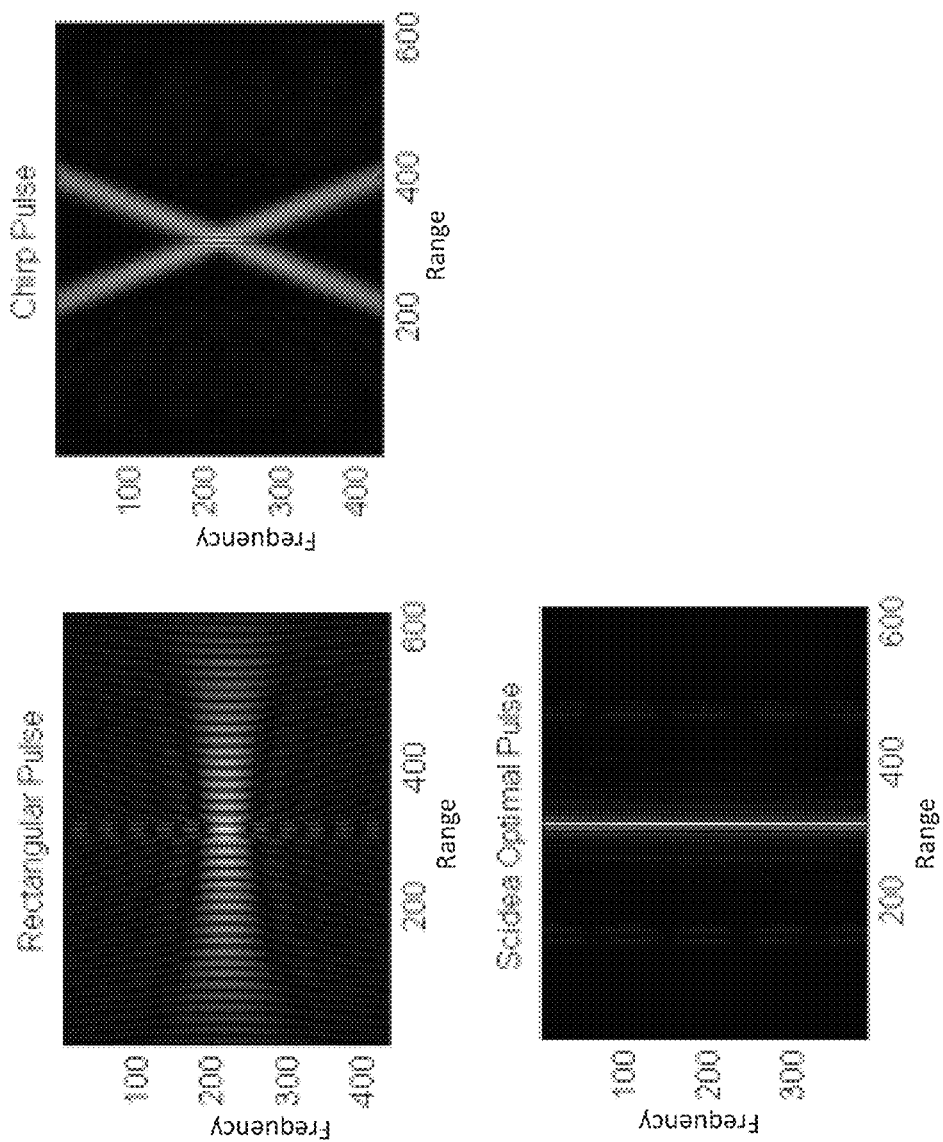
FIG. 16 illustrates plots of the ambiguity functions for the rectangular, chirp, and optimal pulses with the second transducer.
Figure 17:
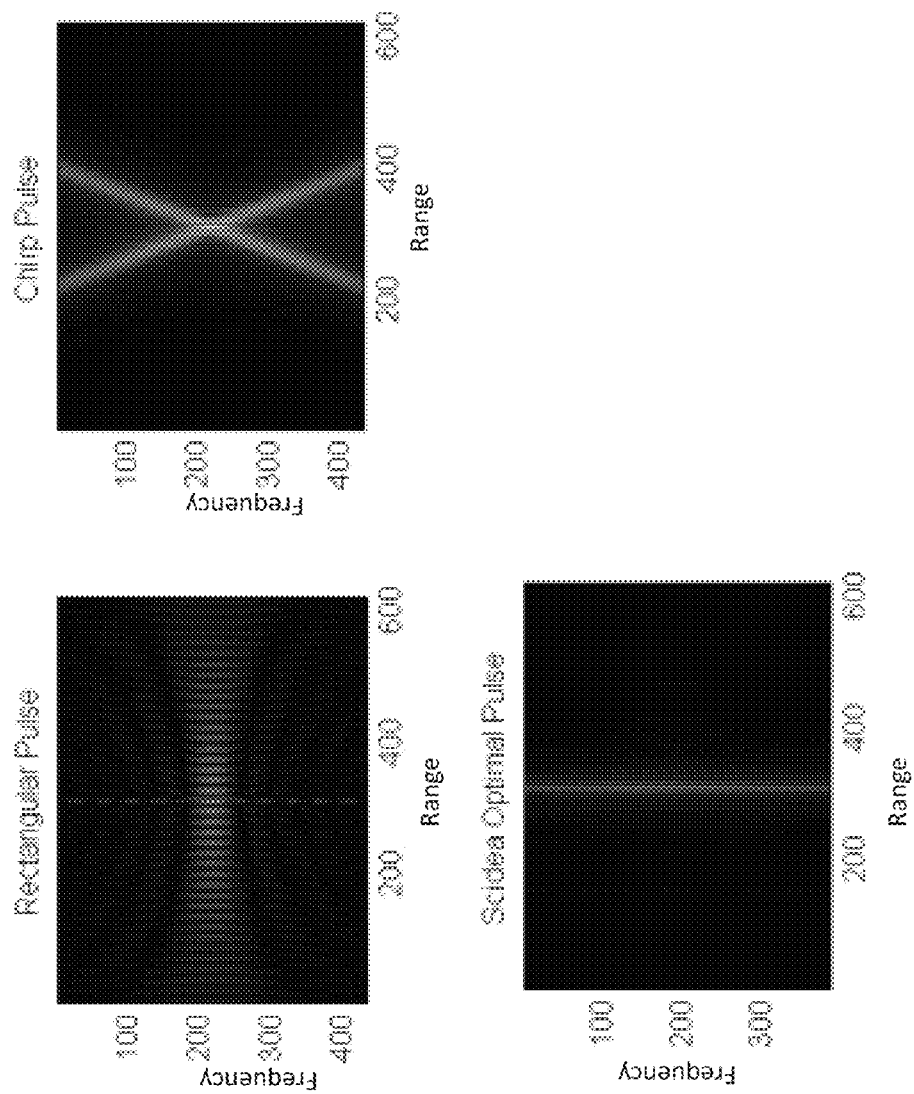
FIG. 17 illustrates plots of the ambiguity functions for the rectangular, chirp, and optimal pulses with the third transducer.

FIGS. 15-17 illustrate the ambiguity functions for the three transducers with the rectangular, chirp, and optimal pulses. FIG. 15 illustrates the ambiguity functions for the first transducer, FIG. 16 illustrates the ambiguity functions for the second transducer, and FIG. 17 illustrates the ambiguity functions for the third transducer. As visible in FIGS. 15-17, the optimal pulse provides the best resolution and also has a lower Doppler dependence than the chirp pulse.

As discussed above, in addition to applications with ultrasound, various embodiments described herein can be used in pulse compression systems for RADAR, LIDAR, SONAR, MRI, CT scans, etc., to name a few examples.

Figure 18:
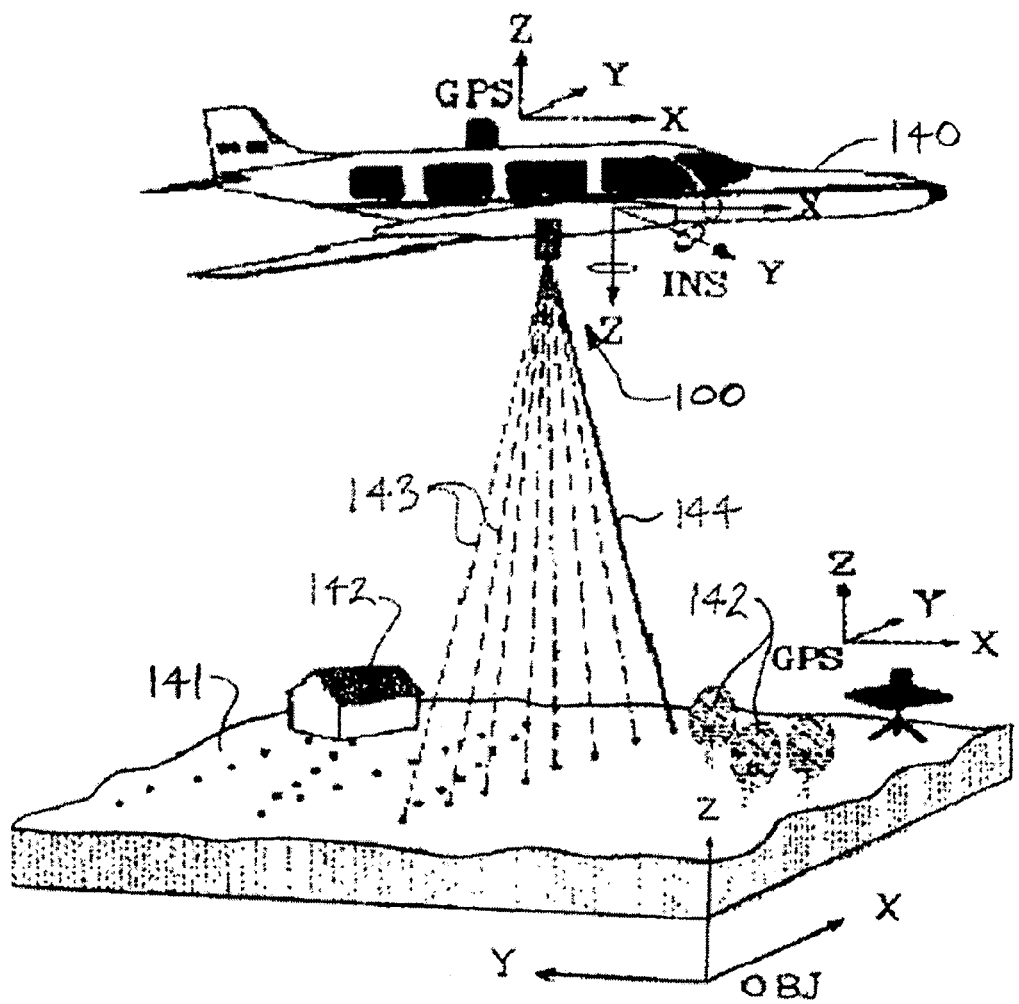
FIG. 18 is a schematic diagram that illustrates implementation of one embodiment of a pulse compression system in imaging targets on the ground from an aircraft.

For example, FIG. 18 is a schematic diagram that illustrates implementation of an embodiment of a pulse compression system 100 using optimized pulses in order to image targets on the ground 141 from an aircraft 140 via LiDAR (Light Detection And Ranging). LiDAR is an optical remote sensing technology that measures properties of scattered light to find range and/or other information of a distant target. The prevalent method to determine distance to an object 142 or surface 141 is to use laser pulses 143. Like radar technology, which uses radio waves, the range to an object 142 is determined by measuring the time delay between transmission of a pulse 143 and detection of the reflected signal 144.

A recent addition to a police officer's speed detection arsenal is LIDAR (Laser Infrared Detection And Ranging). To measure a vehicle's speed, LIDAR determines how long it takes a light pulse to travel from the LIDAR gun to the vehicle and back. From this information, LIDAR can quickly find the distance between the gun and the vehicle. By making several measurements and comparing the distance the vehicle traveled between measurements, LIDAR very accurately determines the vehicle's speed. LIDAR uses a laser beam of invisible infrared light. The beam reflects off any flat surface on the vehicle. Since the beam is very narrow, it is impossible for any laser detector to determine the distance between the LIDAR source and the vehicle.

Just as there are two types of RADAR, there are also two types of lasers: Pulsed Lasers and Continuous Wave (CW) Lasers, which are used in LIDAR applications. The present disclosure includes use of the pulse compression system 100 with optimized pulses for use in ranging and Doppler measurement applications.

Figure 19:
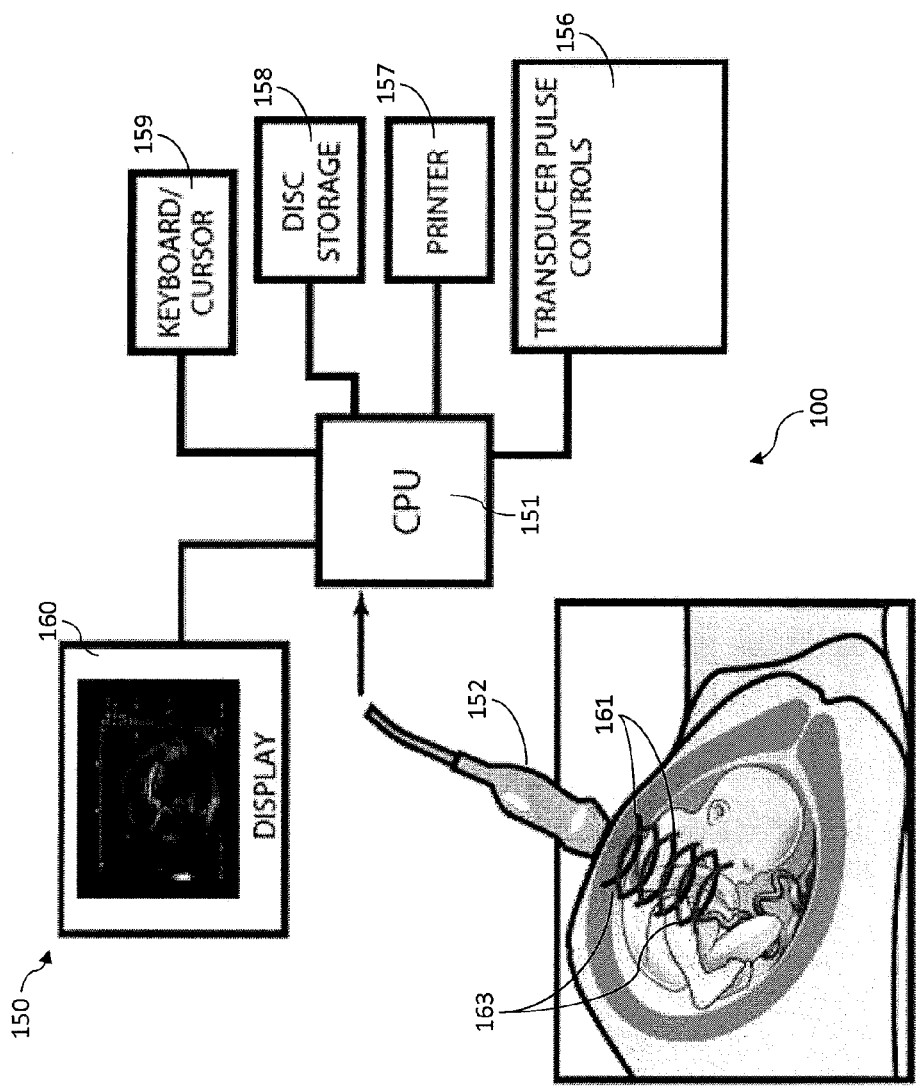
FIG. 19 is a schematic diagram that illustrates implementation of one embodiment of a pulse compression system in an ultrasonic imaging application.

Referring next to FIG. 19 of the drawings, a high-resolution medical ultrasound system 150 which utilizes an illustrative embodiment of the pulse compression system 100 with optimized pulses is illustrated. The system 100 may include an ultrasound transducer 152. As described above, the signal sent to the transducer 152 can be optimized for the particular impulse response of the transducer. In some embodiments, a CPU 151 that can be used to generate an optimal pulse may interface with the ultrasound transducer 152. In some embodiments, the CPU 151 or an additional CPU may be used to correlate signals and generate an image. Additional devices may interface with the CPU 151. The additional devices may include transducer pulse controls 156 (which can be used to modify aspects of the pulse, such as its duration), a printer 157, a disc storage device 158, a keyboard/cursor 159 and/or a display 160, for example and without limitation.

The pulse compression system 100 transmits high frequency sound pulses 161 through the ultrasound transducer 152 into a patient's body 162. The sound pulses 161 travel through the patient's body 162, passing through different types of tissue. Although the average speed of sound through human tissues is 1540 m/s, it does vary with exact tissue type. While the speed of sound through fat is 1459 m/s, it passes through bone at 4080 m/s. When sound encounters two adjacent tissue types with different acoustic properties, a proportion of the sound energy is reflected as reflected sound pulses 163. These boundaries between different tissue types are called acoustic interfaces.

The amount of reflected sound pulses 163 reflected back from an acoustic interface depends on a property of the materials on either side of the interface called acoustic impedance. The acoustic impedance of a material is simply the density of the material multiplied by the speed at which sound travels through the material.

Figure 20:
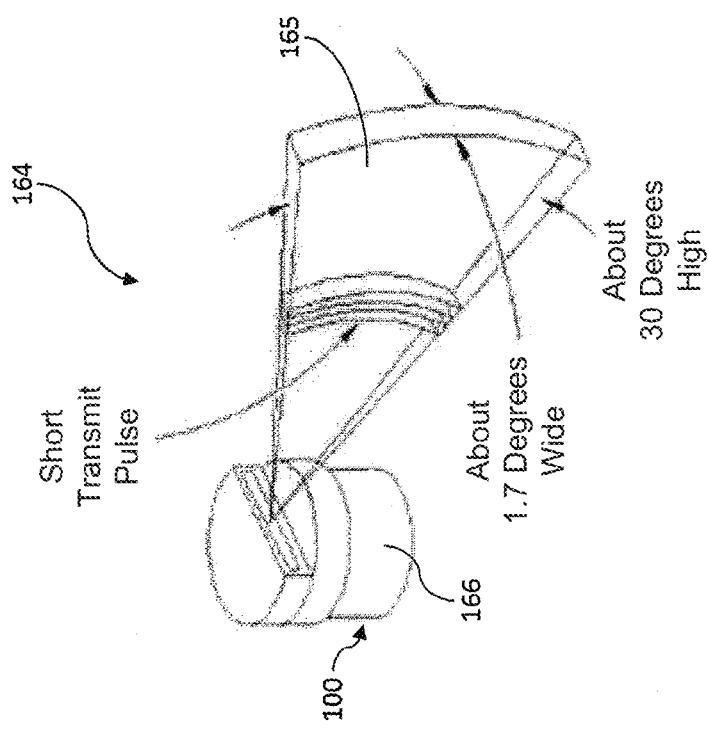
FIG. 20 is a schematic diagram that illustrates implementation of one embodiment of a pulse compression system in a high resolution sonar application.

Referring next to FIG. 20 of the drawings, a high resolution sonar system 164 which utilizes an illustrative embodiment of a pulse compression system 100 is illustrated. As above, the pulse compression system can include the use of an input pulse that is optimized for a particular transducer of the system. The pulse compression system 100 of the high resolution sonar system 164 can be used to power and drive the sonar beam generators 166 of the pulse compression system 100 to emit a sonar pulse 165 which may have a fan shape, as illustrated. The high resolution sonar system 164 uses sound propagation (usually underwater, as in submarine navigation) to navigate, communicate with or detect other vessels. There are two types of technology which share the name "sonar": passive sonar is essentially listening for the sound made by vessels; active sonar is emitting pulses of sounds and listening for echoes. Sonar may be used as a means of acoustic location and of measurement of the echo characteristics of "targets" in the water. Acoustic location in air was used before the introduction of radar.

Figure 21:
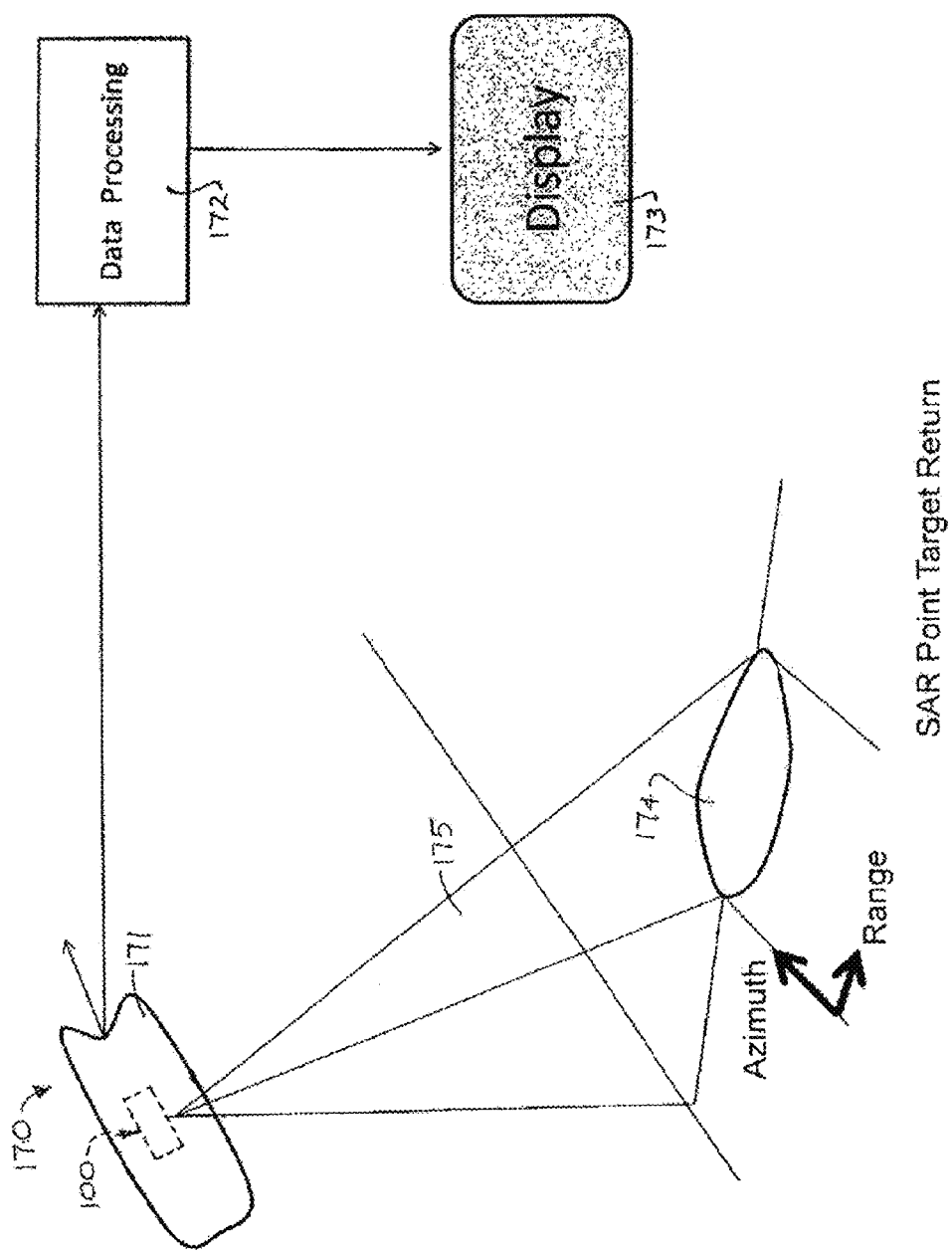
FIG. 21 is a schematic diagram that illustrates implementation of one embodiment of a pulse compression system in a high resolution synthetic aperture application.

Referring next to FIG. 21 of the drawings, a high resolution synthetic aperture radar system 170 which utilizes an illustrative embodiment of a pulse compression system 100 is illustrated. As above, the pulse compression system can generate a pulse that is optimized for the particular components of the system. The pulse compression system 100 may be provided in a spacecraft 171 and emits a high resolution synthetic radar pulse 175 against a target 174. A reflected signal (not illustrated) is reflected from the target 174 back to the pulse compression system 100. A data processor 172 interfaces with or can be included as part of the system 100 and auto-correlates the reflected signal and the emitted high resolution synthetic radar pulse 175. A high resolution image of the target 174 is shown on a display 173 which interfaces with the data processor 172.

Beginning with the launch of SESAT in 1978, Synthetic Aperture Radar (SAR) have provided a wealth of information on such diverse phenomena as surface waves, internal waves, currents, upwelling, shoals, sea ice, wind and rainfall. SAR is the premier sensor for such phenomena because it is sensitive to small surface roughness changes of the order of Radar wavelength (1 millimeter down to several centimeters). It is also independent of solar illumination and is generally unaffected by cloud cover. Most modern RADARs (including SARs) transmit a pulse 175 known as linear modulated waveform and use the standard RADAR principles of range resolution and Doppler shift. Hence the linear FM pulse generator can be replaced with the pulse compression system 100 to produce a higher resolution of SAR images on the display 173.

Figure 22A:
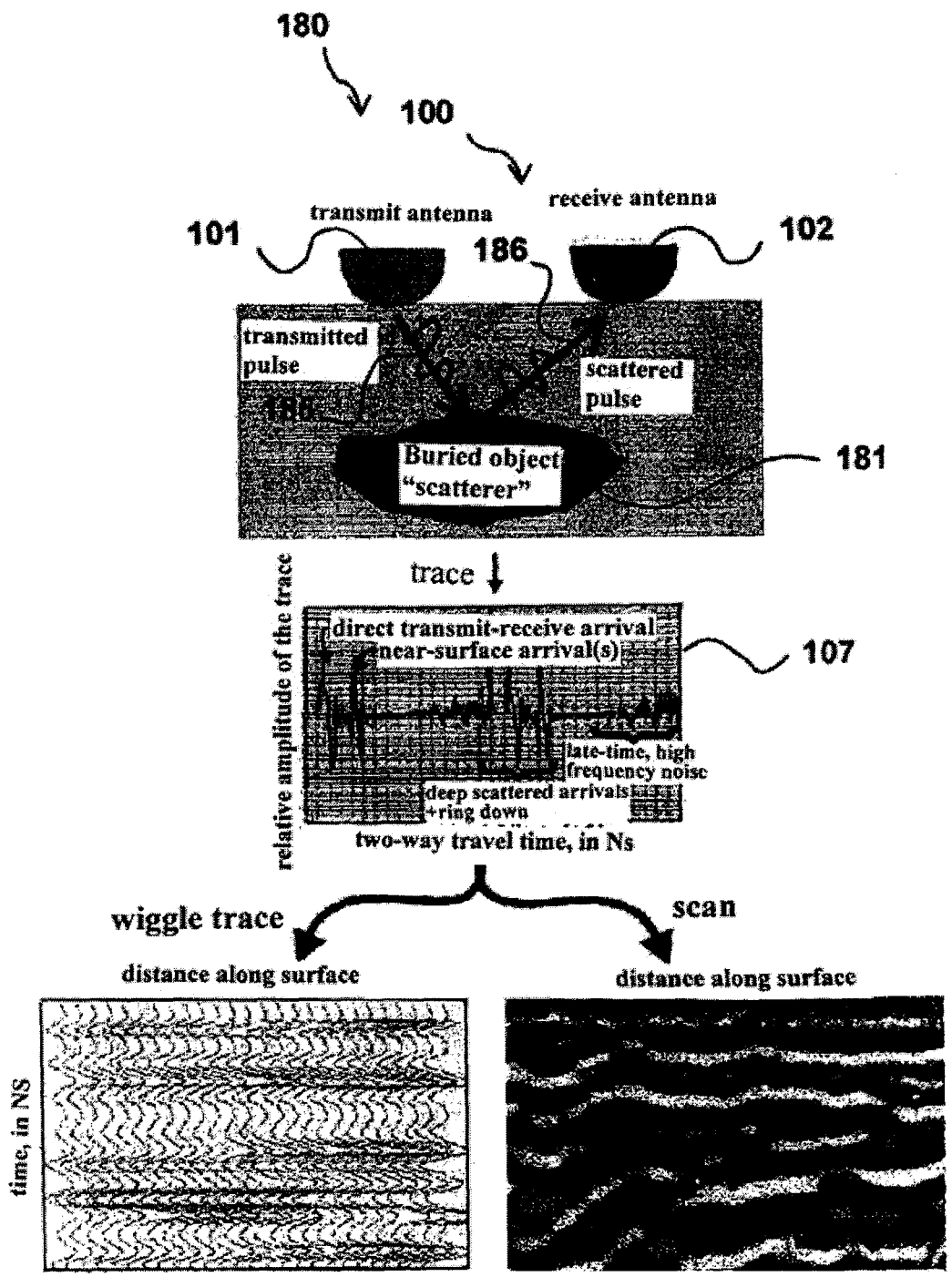
FIGS. 22A-22C are schematic diagrams that illustrate implementation of one embodiment of a pulse compression system in a high resolution ground penetrating radar application.
Figure 22B:
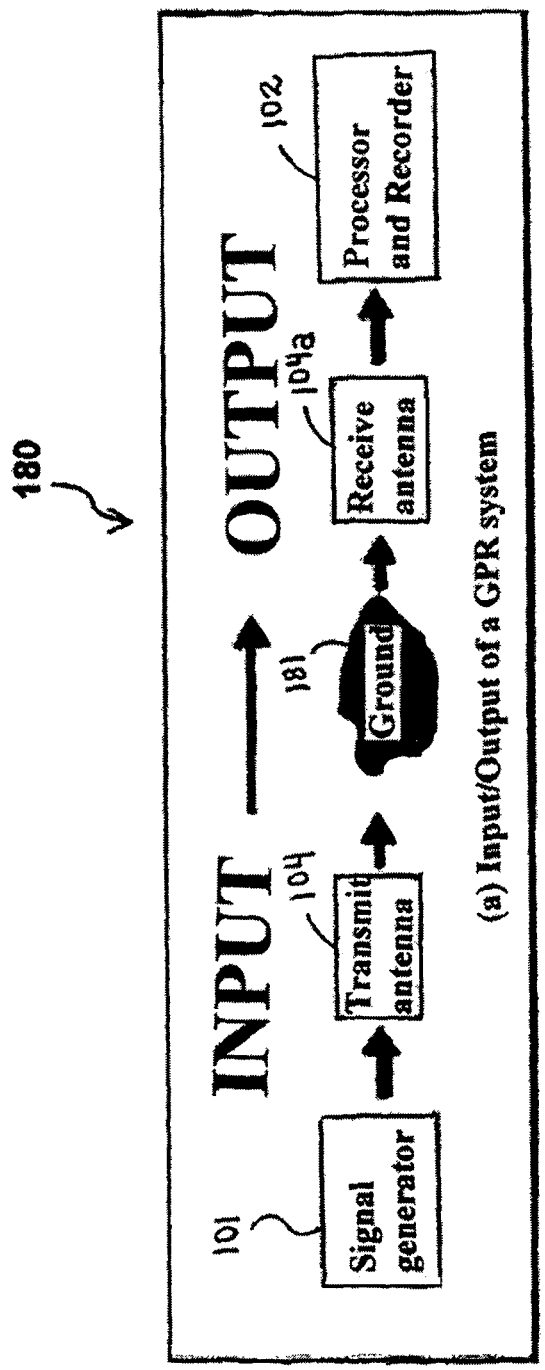
Figure 22C:
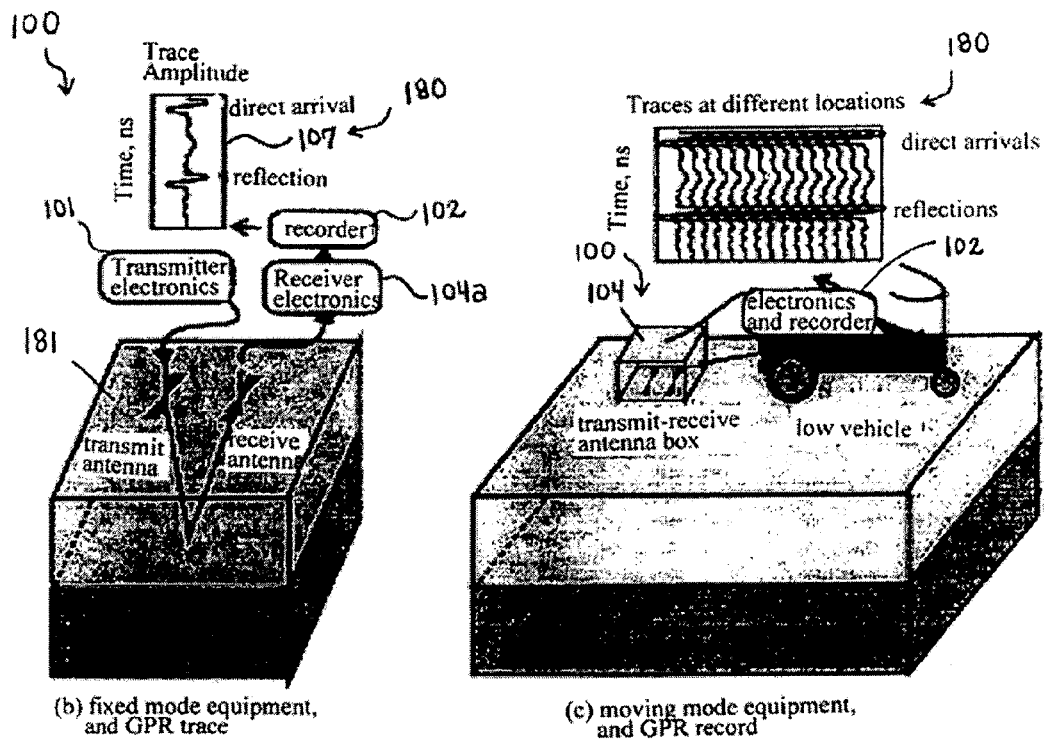

Referring next to FIGS. 22A-22C of the drawings, a high resolution ground penetrating radar system 180 which utilizes an illustrative embodiment of a pulse compression system 100 is illustrated. As above, the pulse compression system can generate a pulse that is optimized for the particular components of the system. Ground Penetrating RADAR (GPR) utilizes a very short burst of radio-frequency energy as a pulse 185 which is transmitted from the non-linear FM transmitter 101 via the transmit antenna 104 (FIG. 22B) of the pulse compression system 100 and radiated into the ground 181 to detect discontinuities in the ground 181. The scattered pulse 186 is reflected from the ground 181 and detected by a receive antenna 104a of the pulse compression system. A signal processor and recorder 102 auto-correlates the scattered pulse 186 and the transmitted pulse 185 and records or displays a high-resolution image of the ground 181 or objects or discontinuities in the ground 181 on a display 107, as illustrated in FIGS. 22A and 22B. Alternative applications of the pulse compression system 100 in implementation of the high resolution ground penetrating radar system 180 are illustrated in FIG. 22C.

The objects or discontinuities in the ground 181 can be cavities, voids, transitions between soil and rock, filled areas and/or buried objects. The performance of conventional GPRs is limited by attenuation of the transmitted pulse in moist soils, especially soils having high clay content. GPRs are used to detect a boundary between rock and air (a cave or cavity) or between one type of soil and another (for example undisturbed soil-to back-filled soil). The strength of the echo signal is dependent on the absorption of the signal to and from the radar to the target, the size and shape of the target, and the degree of discontinuity at the reflecting boundary.

Figure 23:
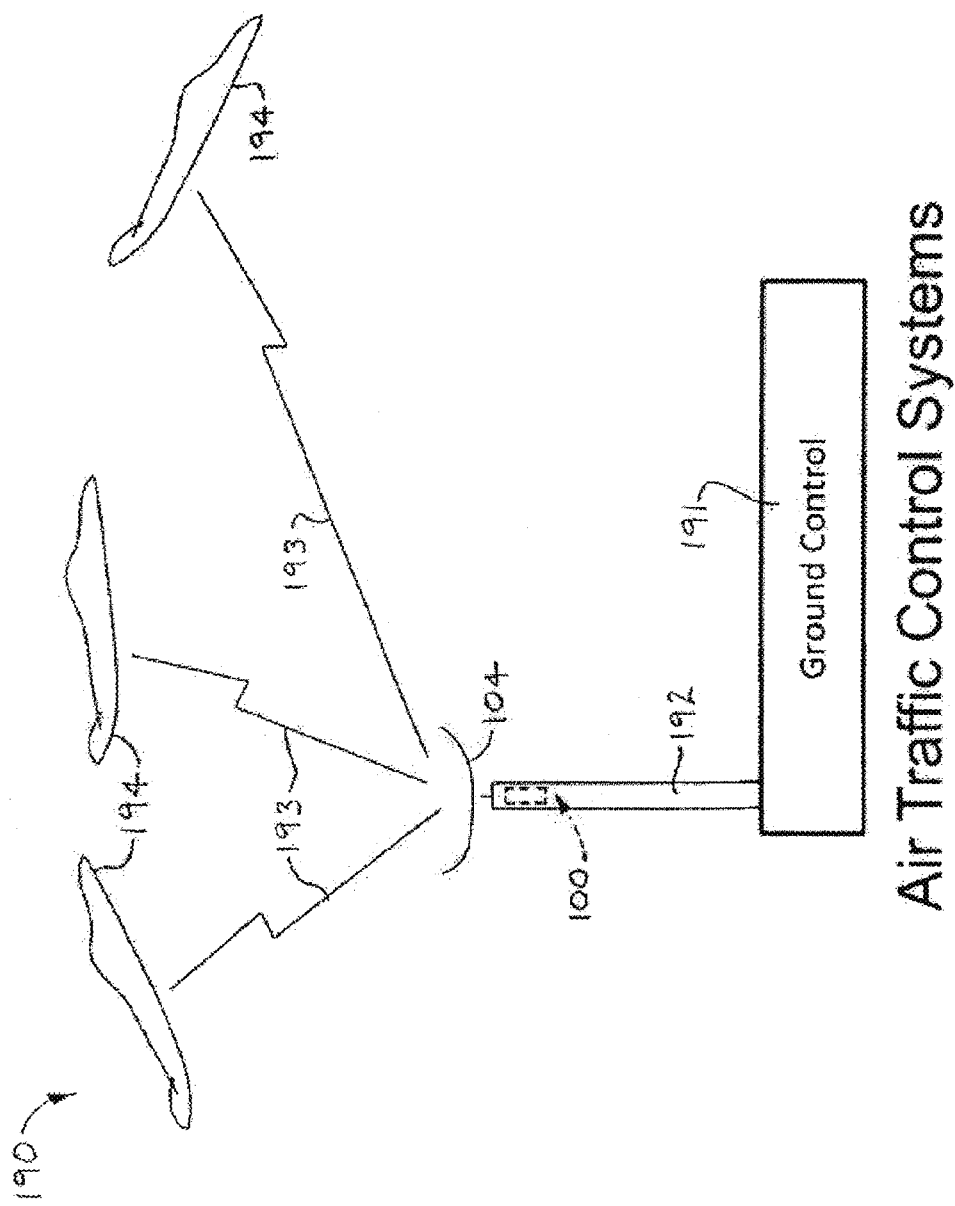
FIG. 23 is a schematic diagram that illustrates implementation of one embodiment of a pulse compression system in a high resolution air traffic control system application.

Referring next to FIG. 23, a high resolution air traffic control system 190 which utilizes an illustrative embodiment of a pulse compression system 100 is illustrated. As above, the pulse compression system can generate a pulse that is optimized for a particular transducer of the system. The air traffic control system 190 may include a ground control 191 having a ground control tower 192. The pulse compression system 100 may be provided in the ground control tower 192. An antenna 104 of the pulse compression system 100 emits pulses 193 which are reflected from flying aircraft 194. Return pulses (not illustrated) reflected from the aircraft 194 are received by the antenna 104 and processed to generate a high-resolution image of the aircraft 194.

Air traffic control systems are critically dependent on the use of RADAR technology for the safety of tens of thousands of aircrafts and millions of passengers every day. With the increase in air traffic, there is need for high resolution air traffic tracking systems. Currently, pulsed radars and FMCW radars are used for range measurement and Doppler measurements. With the use of the non-linear FM pulse compression system 100, the performance of the air traffic systems 190 can be significantly improved with more accurate estimation and detection of aircraft 194. In particular, the relative positions of those aircraft 194 which would otherwise come within dangerously close proximity to each other may be detected sufficiently early to prevent such close proximity and avert potential aviation accidents.

In addition to providing improved range and temporal resolution for a variety of applications, the systems and methods described herein for providing an optimized pulse can increase the flexibility of particular systems by providing for a pulse that depends on the particular transducer. Thus, where current systems are configured to generate pulses for transducers that meet a certain spectral range, transducers that are produced outside of that range (resulting, for example, from manufacturing errors) are not considered usable. The systems and methods described herein, however, allow for the optimized use of any functioning transducer. By allowing for the use of transducers that may otherwise be considered faulty, there can be less waste of transducers not considered to meet quality control requirements.

Computing System

Figure 24:
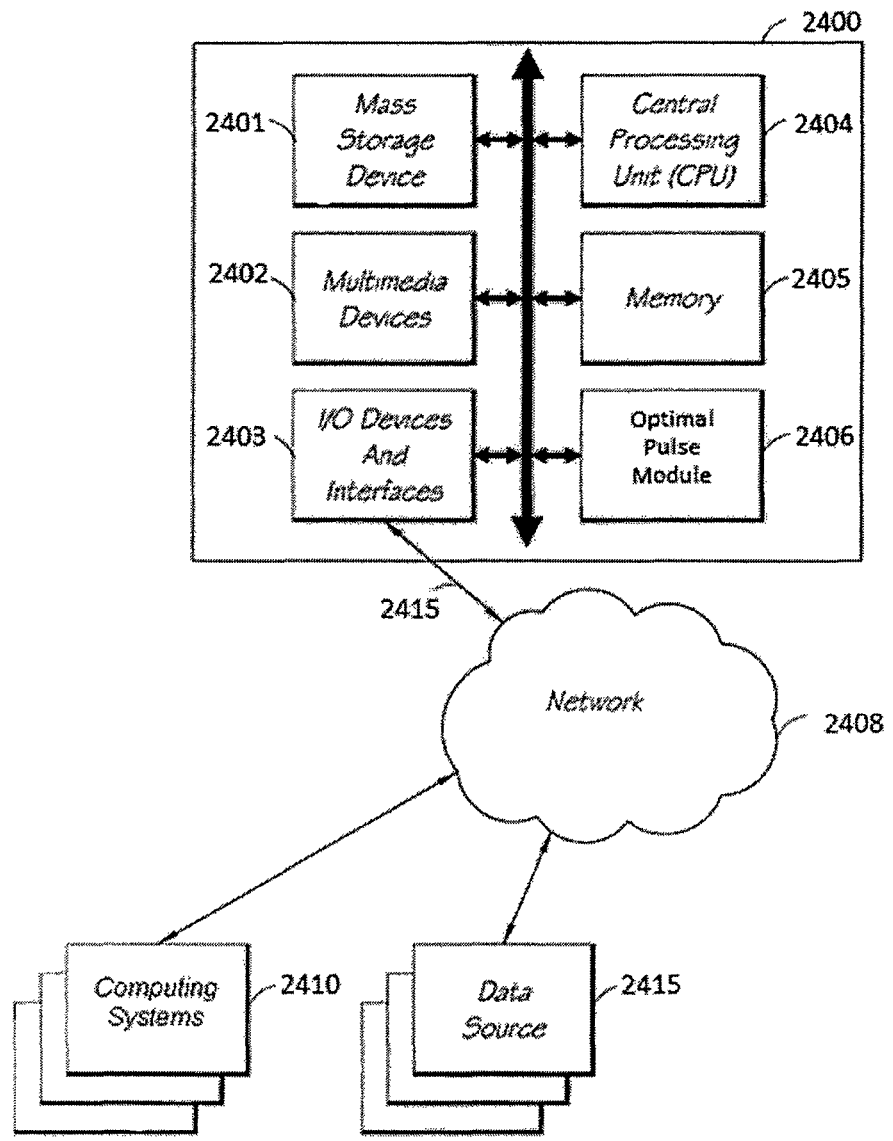
FIG. 24 is a block diagram depicting one embodiment of a computer hardware system configured to implement one or more embodiments of the pulse compression systems described herein.

In some embodiments, the various pulse compression systems described above can include a computing system 2400 system as illustrated in FIG. 24, which is a block diagram of one embodiment of a computing system. In some embodiments, the computing system 2400 can be in communication with one or more computing systems 2410 and/or one or more data sources 2415 via one or more networks 2408. The computing system 2400 may be used to implement one or more of the systems and methods described herein. For example, in some embodiments, the computing system 2400 may be configured to generate one or more of the optimal pulses described herein. While FIG. 24 illustrates one embodiment of a computing system 2400, it is recognized that the functionality provided for in the components and modules of computing system 2400 may be combined into fewer components and modules or further separated into additional components and modules.

Modules

In some embodiments, the system 2400 comprises an optimal pulse module 2406 that carries out the functions described herein with reference to generating an optimal pulse, including any one of the methods described above. The optimal pulse module 2406 may be executed on the computing system 2400 by a central processing unit 2404 discussed further below. In some embodiments, one or more of the computing systems 2400, 2410 can comprise a data processing module that carries out various correlation and image generation functions described herein.

In general, the word "module," as used herein, refers to logic embodied in hardware or firmware, or to a collection of software instructions, possibly having entry and exit points, written in a programming language, such as, for example, COBOL, CICS, Java, Lua, C or C++. A software module may be compiled and linked into an executable program, installed in a dynamic link library, or may be written in an interpreted programming language such as, for example, BASIC, Perl, or Python. It will be appreciated that software modules may be callable from other modules or from themselves, and/or may be invoked in response to detected events or interrupts. Software instructions may be embedded in firmware, such as an EPROM. It will be further appreciated that hardware modules may be comprised of connected logic units, such as gates and flip-flops, and/or may be comprised of programmable units, such as programmable gate arrays or processors. The modules described herein are preferably implemented as software modules, but may be represented in hardware or firmware. Generally, the modules described herein refer to logical modules that may be combined with other modules or divided into sub-modules despite their physical organization or storage.

Computing System Components

In some embodiments, the computing system 2400 also comprises a mainframe computer suitable for controlling and/or communicating with large databases, performing high volume transaction processing, and generating reports from large databases. The computing system 2400 also comprises a central processing unit ("CPU") 2404, which may comprise a conventional microprocessor. The computing system 2400 further comprises a memory 2405, such as random access memory ("RAM") for temporary storage of information and/or a read only memory ("ROM") for permanent storage of information, and can include a mass storage device 2401, such as a hard drive, diskette, or optical media storage device. Typically, the modules of the computing system 2400 are connected to the computer using a standards based bus system. In different embodiments, the standards based bus system could be Peripheral Component Interconnect (PCI), Microchannel, SCSI, Industrial Standard Architecture (ISA) and Extended ISA (EISA) architectures, for example.

In some embodiments, the computing system 2400 can include one or more commonly available input/output (I/O) devices and interfaces 2403, such as a keyboard, mouse, touchpad, and printer. In one embodiment, the I/O devices and interfaces 2403 comprise one or more display devices, such as a monitor, that allows the visual presentation of data to a user. More particularly, a display device provides for the presentation of GUIs, application software data, and multimedia presentations, for example. In the embodiment of FIG. 24, the I/O devices and interfaces 2403 also provide a communications interface to various external devices. The computing system 2400 may also comprise one or more multimedia devices 2402, such as speakers, video cards, graphics accelerators, and microphones, for example.

Computing System Device/Operating System

The computing system 2400 may run on a variety of computing devices, such as, for example, a server, a Windows server, a Structure Query Language server, a Unix server, a personal computer, a mainframe computer, a laptop computer, a cell phone, a personal digital assistant, a kiosk, an audio player, and so forth. The computing system 2400 is generally controlled and coordinated by operating system software, such as z/OS, Windows 95, Windows 98, Windows NT, Windows 2000, Windows XP, Windows Vista, Windows 7, Linux, BSD, SunOS, Solaris, or other compatible operating systems. In Macintosh systems, the operating system may be any available operating system, such as MAC OS X. In other embodiments, the computing system 2400 may be controlled by a proprietary operating system. Conventional operating systems control and schedule computer processes for execution, perform memory management, provide file system, networking, and I/O services, and provide a user interface, such as a graphical user interface ("GUI"), among other things.

Network

In the embodiment of FIG. 24, the computing system 2400 is coupled to a network 2408, such as a LAN, WAN, or the Internet, for example, via a wired, wireless, or combination of wired and wireless, communication link 2415. The network 2408 communicates with various computing devices and/or other electronic devices via wired or wireless communication links. In the embodiment of FIG. 24, the network 2408 is communicating with one or more computing systems 2410 and/or one or more data sources 2415.

Access to the optimal pulse module 2406 of the computer system 2400 by computing systems 2410 and/or by data sources 2415 may be through a web-enabled user access point such as the computing systems' 2410 or data source's 2415 personal computer, cellular phone, laptop, or other device capable of connecting to the network 2408. Such a device may have a browser module is implemented as a module that uses text, graphics, audio, video, and other media to present data and to allow interaction with data via the network 2408.

The browser module may be implemented as a combination of an all points addressable display such as a cathode-ray tube (CRT), a liquid crystal display (LCD), a plasma display, or other types and/or combinations of displays. In addition, the browser module may be implemented to communicate with input devices 2403 and may also comprise software with the appropriate interfaces which allow a user to access data through the use of stylized screen elements such as, for example, menus, windows, dialog boxes, toolbars, and controls (for example, radio buttons, check boxes, sliding scales, and so forth). Furthermore, the browser module may communicate with a set of input and output devices to receive signals from the user.

The input device(s) may comprise a keyboard, roller ball, pen and stylus, mouse, trackball, voice recognition system, or pre-designated switches or buttons. The output device(s) may comprise a speaker, a display screen, a printer, or a voice synthesizer. In addition a touch screen may act as a hybrid input/output device. In another embodiment, a user may interact with the system more directly such as through a system terminal connected to the score generator without communications over the Internet, a WAN, or LAN, or similar network.

In some embodiments, the system 2400 may comprise a physical or logical connection established between a remote microprocessor and a mainframe host computer for the express purpose of uploading, downloading, or viewing interactive data and databases on-line in real time. The remote microprocessor may be operated by an entity operating the computer system 2400, including the client server systems or the main server system, and/or may be operated by one or more of the data sources 2415 and/or one or more of the computing systems. In some embodiments, terminal emulation software may be used on the microprocessor for participating in the micro-mainframe link.

In some embodiments, computing systems 2410 that are internal to an entity operating the computer system 2400 may access the optimal pulse module 2406 internally as an application or process run by the CPU 2404.

User Access Point

In an embodiment, a user access point or user interface 2403 comprises a personal computer, a laptop computer, a cellular phone, a GPS system, a Blackberry® device, a portable computing device, a server, a computer workstation, a local area network of individual computers, an interactive kiosk, a personal digital assistant, an interactive wireless communications device, a handheld computer, an embedded computing device, or the like.

Other Systems

In addition to the systems that are illustrated in FIG. 24, the network 2408 may communicate with other data sources or other computing devices. The computing system 2400 may also comprise one or more internal and/or external data sources. In some embodiments, one or more of the data repositories and the data sources may be implemented using a relational database, such as DB2, Sybase, Oracle, CodeBase and Microsoft® SQL Server as well as other types of databases such as, for example, a signal database, an object-oriented database, and/or a record-based database.

The terms "approximately", "about", and "substantially" as used herein represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In addition, while a number of variations of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. Accordingly, it should be understood that various features and aspects of the disclosed embodiments can be combined with or substituted for one another in order to form varying modes of the disclosed invention. Thus, it is intended that the scope of the present invention herein disclosed should not be limited by the particular disclosed embodiments described above.

Similarly, this method of disclosure is not to be interpreted as reflecting an intention that any claim require more features than are expressly recited in that claim. Rather, inventive aspects may lie in a combination of fewer than all features of any single foregoing disclosed embodiment. Thus, the claims following the Detailed Description are hereby expressly incorporated into this Detailed Description, with each claim standing on its own as a separate embodiment.

What is claimed is:

1. A pulse compression system, the system comprising:
an antenna configured to produce a first analog signal for transmission toward a target, the antenna configured to receive a second analog signal reflected from the target and convert the second analog signal into a digital received signal, wherein the antenna comprises an impulse response that represents characteristics of the antenna;
a signal generator coupled to an input of the antenna, the signal generator configured to generate an initial signal based on the impulse response of the antenna, wherein the signal generator receives an indication of the impulse response of the antenna from the antenna, and wherein the signal generator generates the initial signal in a manner that reduces noise introduced by the antenna into the digital received signal when the antenna converts the second analog signal into the digital received signal from a first level to a second level that is lower than the first level;
a data processing engine coupled to the antenna, the data processing engine configured to receive the digital received signal from the antenna, the data processing engine further configured to correlate the digital received signal with the initial signal; and
an image generator configured to generate an image based on the correlation of the digital received signal with the initial signal.

2. The pulse compression system of claim 1, further comprising a display configured to display the generated image to a user.

3. The pulse compression system of claim 1, wherein the signal generator is configured to generate the initial signal based on a convolution of the impulse response of the antenna with the impulse response of the antenna.

4. The pulse compression system of claim 1, wherein the initial signal is a pulse signal.

5. The pulse compression system of claim 4, wherein the pulse signal is calculated based on a Gaussian function having a standard deviation between 1 and 3.

6. The pulse compression system of claim 5, wherein the Gaussian function has a standard deviation of 2.5.

7. The pulse compression system of claim 4, wherein the pulse signal comprises a threshold value that is between approximately 0.01% of an absolute value of a Fast Fourier Transform of the indication of the impulse response of the antenna and approximately 10% of an absolute value of the Fast Fourier Transform of the indication of the impulse response of the antenna.

8. The pulse compression system of claim 7, wherein the threshold value is equal to 0.1% of the absolute value of a Fast Fourier Transform of the indication of the impulse response of the antenna.

9. The pulse compression system of claim 1, wherein the signal generator is configured to transmit the initial signal to the antenna for production as the first analog signal.

10. A pulse compression system, the pulse compression system comprising:
an operations component configured to receive a first digital signal, convert the first digital signal into an analog signal and transmit the analog signal toward a target, receive a reflected signal from the target, and convert the reflected signal into a second digital signal, wherein the operations component comprises an impulse response that represents characteristics of the operations component;
a pulse generator coupled to an input of the operations component, the pulse generator configured to generate the first digital signal based on the impulse response of the operations component, wherein the pulse generator receives an indication of the impulse response of the operations component from the operations component, and wherein the pulse generator generates the first digital signal in a manner that reduces noise introduced by the operations component into the second digital signal when the operations component converts the reflected signal into the second digital signal from a first level to a second level that is lower than the first level; and
a processor configured to correlate the second digital signal with the first digital signal to generate an image.

11. The pulse compression system of claim 10, further comprising a display configured to display the image.

12. The pulse compression system of claim 10, wherein the operations component comprises a first antenna configured to convert the first digital signal to the analog signal and transmit the analog signal toward the target, wherein the first antenna comprises a first impulse response that represents characteristics of the first antenna.

13. The pulse compression system of claim 12, wherein the first antenna is further configured to receive the reflected signal from the target and convert the reflected signal into the second digital signal.

14. The pulse compression system of claim 13, wherein the pulse generator is configured to generate the first digital signal based on a convolution of the first impulse response with the first impulse response.

15. The pulse compression system of claim 12, wherein the operations component further comprises a second antenna configured to receive the reflected signal from the target and convert the reflected signal into the second digital signal, wherein the second antenna comprises a second impulse response that represents characteristics of the second antenna.

16. The pulse compression system of claim 15, wherein the pulse generator is configured to generate the first digital signal based on a convolution of the first impulse response with the second impulse response.

17. The pulse compression system of claim 10, wherein the first digital signal is a pulse signal, and wherein the pulse signal is determined based on a Gaussian function.

18. The pulse compression system of claim 10, wherein the first analog signal is one of a RADAR signal, an ultrasound signal, an MRI signal, or a CT signal.

19. The pulse compression system of claim 10, wherein the target is one of an object on ground, an object in air, or an underwater object.

20. The pulse compression system of claim 10, wherein the pulse compression system is one of an ultrasound system, a RADAR system, a LiDAR system, a SONAR system, or an MRI system.

* * * * *